United States Patent
Flom et al.

[11] Patent Number: 5,904,711
[45] Date of Patent: May 18, 1999

[54] EXPANDABLE THORACOSCOPIC DEFIBRILLATION CATHETER SYSTEM AND METHOD

[75] Inventors: James R. Flom, Palo Alto; Scott H. Miller, Sunnyvale; Gregory G. Ulrich, Mission Viejo, all of Calif.

[73] Assignee: Heartport, Inc., Redwood City, Calif.

[21] Appl. No.: 08/598,670

[22] Filed: Feb. 8, 1996

[51] Int. Cl.⁶ .............................. A61N 1/05; A61N 1/39
[52] U.S. Cl. .......................................... 607/129; 607/119
[58] Field of Search ................................ 607/5, 115, 116, 607/119, 129, 148

[56] References Cited

U.S. PATENT DOCUMENTS

| | | | |
|---|---|---|---|
| 2,985,172 | 8/1961 | Jones | 128/116 |
| 4,231,365 | 11/1980 | Scarberry | 128/207.15 |
| 4,270,549 | 6/1981 | Hellman | 607/129 |
| 4,351,330 | 9/1982 | Scarberry | 128/207.15 |
| 4,567,900 | 2/1986 | Moore | 128/784 |
| 4,628,937 | 12/1986 | Hess et al. | 128/642 |
| 4,640,298 | 2/1987 | Pless et al. | 128/784 |
| 4,706,688 | 11/1987 | Michael et al. | 128/785 |
| 4,735,206 | 4/1988 | Hewson | 128/419 |
| 4,765,341 | 8/1988 | Mower et al. | 128/785 |
| 4,884,567 | 12/1989 | Elliott et al. | 606/126 |
| 4,974,595 | 12/1990 | Nordenstrom | 128/642 |
| 5,033,477 | 7/1991 | Chin et al. | 128/765 |
| 5,052,390 | 10/1991 | Hewson | 128/419 D |
| 5,195,505 | 3/1993 | Josefsen | 128/20 |
| 5,213,113 | 5/1993 | Hlinsky | 128/800 |
| 5,249,574 | 10/1993 | Bush et al. | 607/9 |
| 5,295,481 | 3/1994 | Geeham | 601/43 |
| 5,327,909 | 7/1994 | Kiser et al. | 607/129 |
| 5,336,252 | 8/1994 | Cohen | 607/119 |
| 5,370,650 | 12/1994 | Tovey et al. | 606/151 |
| 5,370,685 | 12/1994 | Stevens | 623/2 |
| 5,381,788 | 1/1995 | Matula et al. | 128/20 |
| 5,387,234 | 2/1995 | Hirschberg | 607/129 |
| 5,391,200 | 2/1995 | KenKnight et al. | 607/129 |
| 5,397,336 | 3/1995 | Hirschberg et al. | 607/6 |
| 5,397,341 | 3/1995 | Hirschberg et al. | 607/122 |
| 5,411,546 | 5/1995 | Bowald et al. | 607/119 |
| 5,411,547 | 5/1995 | Causey, III | 607/129 |
| 5,464,447 | 11/1995 | Fogarty et al. | 607/129 |
| 5,545,202 | 8/1996 | Dahl et al. | 607/116 |
| 5,571,074 | 11/1996 | Buckman, Jr. et al. | 601/6 |
| 5,618,287 | 4/1997 | Fogarty et al. | 607/5 |

FOREIGN PATENT DOCUMENTS 0 665 030 A2   1/1995   European Pat. Off. ......... A61N 1/05

OTHER PUBLICATIONS

Cardiac Defibrillator Devices, p. 4, (1989).

*Primary Examiner*—George Manuel
*Assistant Examiner*—Carl H. Layno
*Attorney, Agent, or Firm*—Jeffry J. Grainger; Jens E. Hoekendijk

[57] ABSTRACT

Methods and apparatus for thoracoscopic defibrillation of a patient's heart. The technique involves introducing a first electrode (10) through a percutaneous intercostal penetration, positioning the first electrode against the heart surface (H) and positioning a second electrode (10') against the patient's body. A voltage is then applied through the percutaneous intercostal penetration to the first electrode and to a second electrode to deliver electrical energy to the first electrode, through at least a portion of the patient's heart, and to the second electrode. The electrical energy applies an electric charge to the patient's heart to defibrillate the heart muscle or restart the heart during, for example, cardiac procedures that involve arresting the heart.

66 Claims, 19 Drawing Sheets

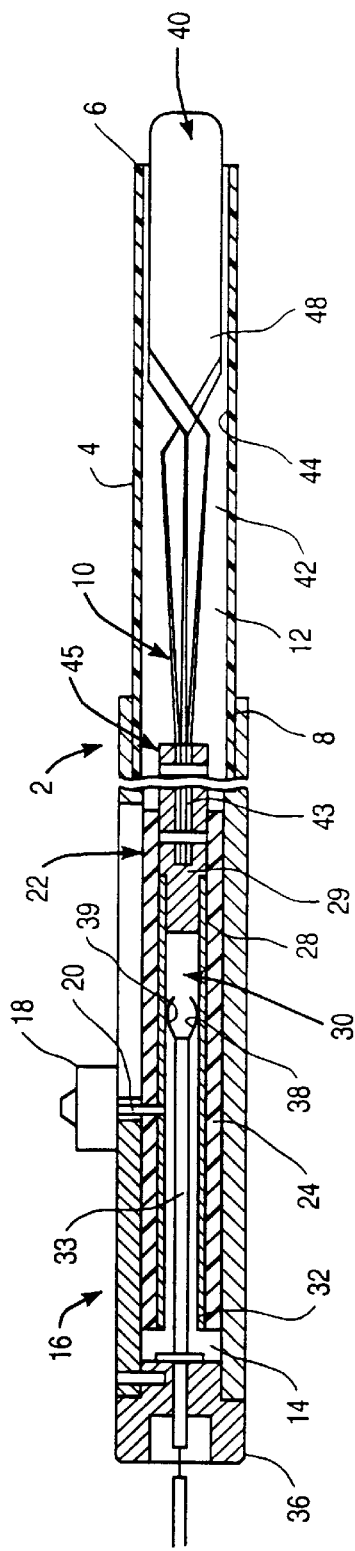
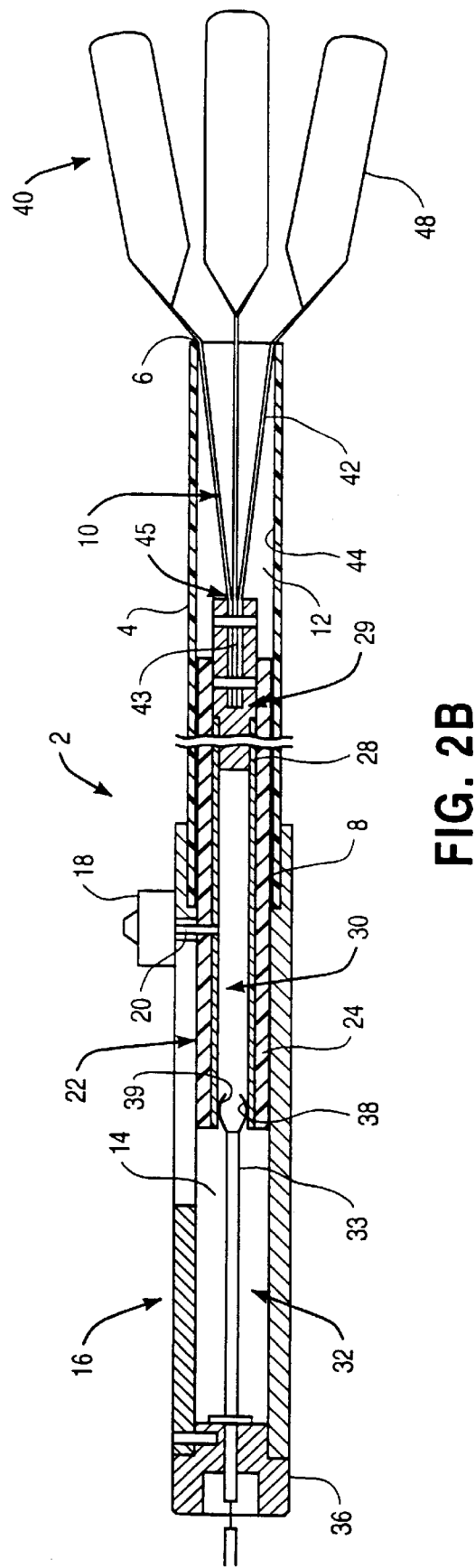
FIG. 2A
FIG. 2B

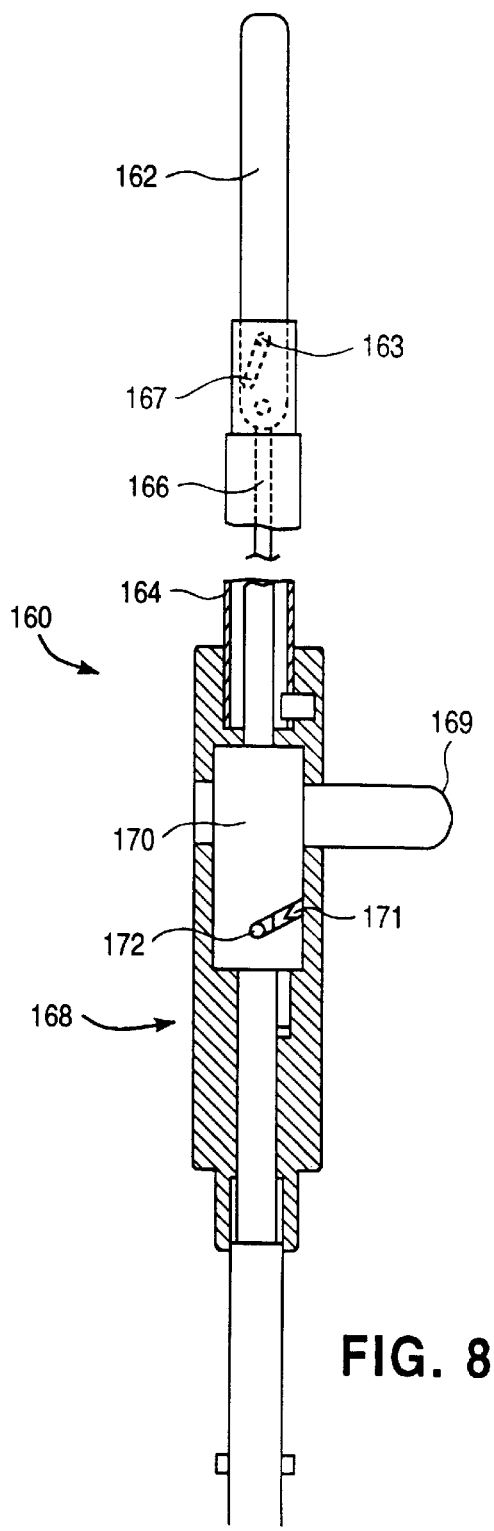
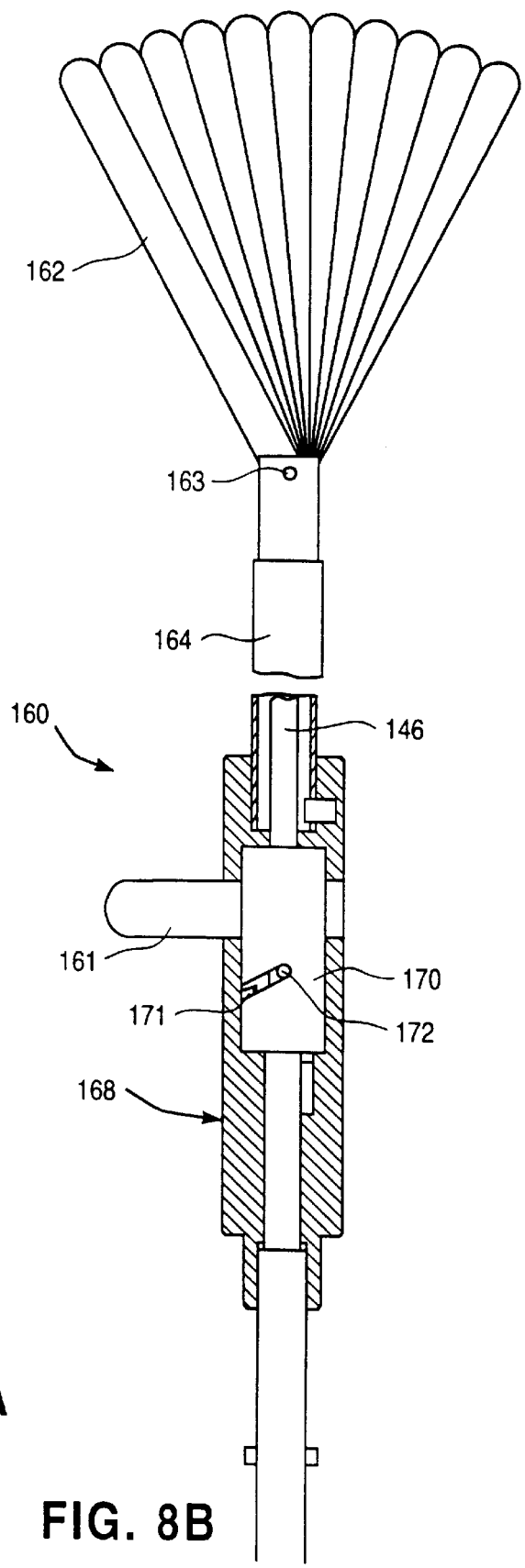
FIG. 8A
FIG. 8B

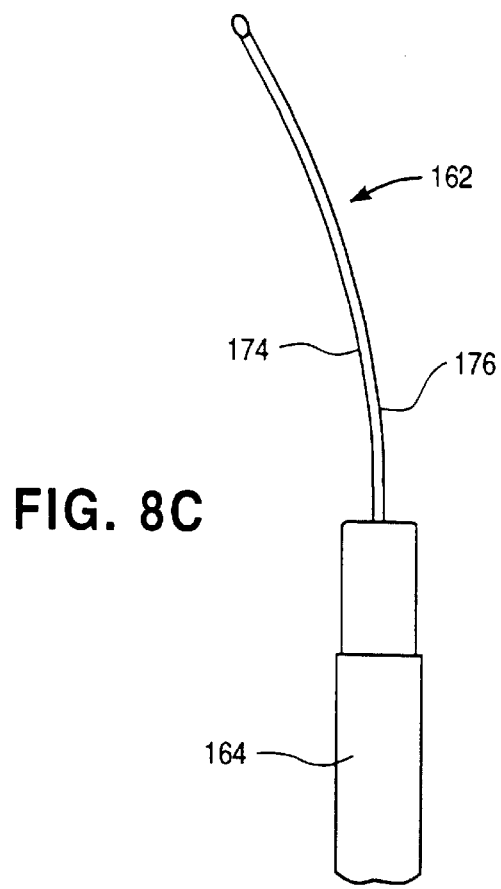
FIG. 8C
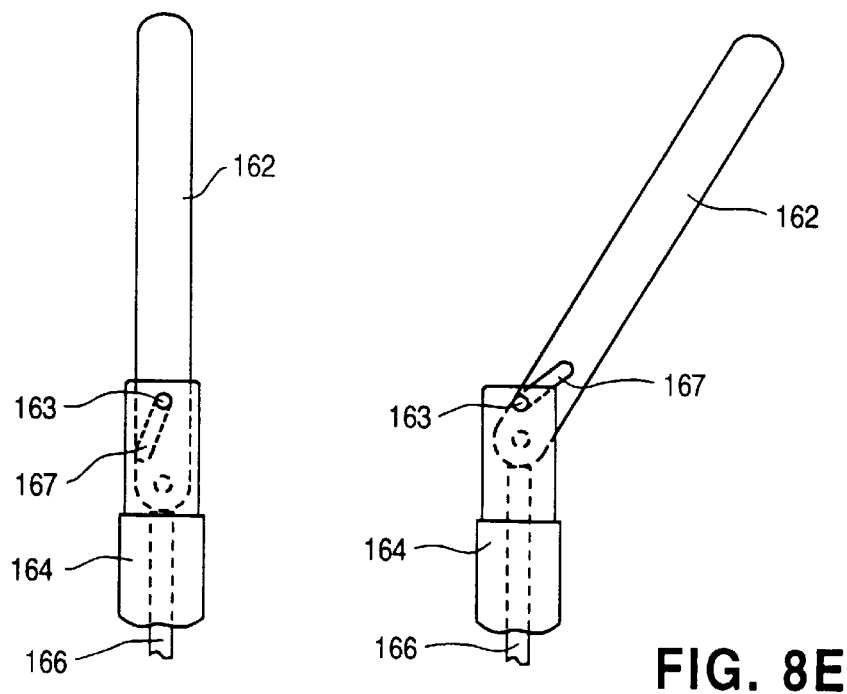
FIG. 8D
FIG. 8E

EXPANDABLE THORACOSCOPIC DEFIBRILLATION CATHETER SYSTEM AND METHOD

FIELD OF THE INVENTION

This invention relates generally to a system and method for performing less-invasive surgical procedures, and more specifically, to a system and method for defibrillating and/or restarting the heart during the course of a thoracoscopic cardiac procedure.

BACKGROUND OF THE INVENTION

Cardiac arrhythmias, such as atrial or ventricular fibrillation, usually occur when the electrical signals that stimulate the heart muscles are not properly conducted so that they produce rapid, erratic excitation known as fibrillation, without coordinated contraction or expansion of the ventricles and atrium. Cardiac arrhythmias can be overcome by applying a charge of electrical energy to the fibrillating myocardial tissue. This procedure, know as either cardioversion or defibrillation, is typically accomplished by applying electrical pulses through large paddle-shaped electrodes positioned against the chest of a patient or, during the course of open cardiac surgery, applied directly to the patient's heart tissue. The electric current passes through the patient's heart and overrides or repolarizes the erratic voltages in the fibrillating heart tissue so that the electrical signals are reorganized, causing the heart to beat in a normal rhythm, commonly known as a "sinus rhythm".

Defibrillation techniques may also be necessary to artificially restart the patient's heart during cardiac procedures that involve arresting the heart for a period of time during the procedure. Conventional cardiac surgery typically requires that the patient's sternum be divided longitudinally and the chest be spread apart to provide access to the heart, an access technique known as a median sternotomy. The heart is isolated from the arterial system by introducing an external aortic cross-clamp through the sternotomy and applying it to the aorta between the brachiocephalic artery and the coronary ostia. While the patient's heart is arrested using cold cardioplegic agents and the patient is supported by cardiopulmonary bypass, the surgical team may perform an operation directly on the arrested heart, such as coronary artery bypass grafting, repair and replacement of mitral, aortic, and other heart valves, repair of atrial and ventricular septal defects, pulmonary thrombectomy, treatment of aneurysms, electrophysiological mapping and ablation of the myocardium, and the like. When the surgery has been completed, the patient's heart is restarted by discontinuing infusion of cardioplegic agents, and removing the aortic clamp from the ascending aorta to allow blood to warm the heart. In some cases, however, the patient's heart does not automatically restart and the surgical team must artificially prompt the heart using cardioversion or defibrillation. Paddle-shaped electrodes are placed directly on the heart through the median sternotomy and an electrical charge is delivered to the heart muscle through the electrodes.

While effective in many cases, conventional open heart surgical techniques are highly traumatic to the patient due to the necessity of a median sternotomy or other form of gross thoracotomy. Therefore, new methods of performing surgery on the heart using minimally-invasive techniques have been recently developed. In these methods, the patient's heart is arrested by occluding the patient's aorta between the coronary arteries and the brachiocephalic artery with an expandable balloon on the distal end of an endovascular catheter introduced via a femoral artery. Cardioplegic fluid is then delivered to the patient's myocardium through a lumen in the same catheter or through a separate catheter positioned in the coronary sinus. This method allows the surgeon to perform operations directly on the heart without creating a large opening in the patient's chest. A complete description of such methods is found in commonly assigned, co-pending application Ser. No. 08/282,192, now U.S. Pat. Nos. 5,584,803 filed Jul. 28, 1994, and 5,452,733, which are hereby incorporated herein by reference.

This new generation of thoracoscopic methods of performing heart surgery has, of course, created many new challenges. One such challenge arises when the heart must be artificially restarted by defibrillation during or after the cardiac procedure. The large opening in the chest typically produced by the median sternotomy is not available for placement of the electrodes onto the heart. Instead, the electrodes must be introduced in a minimally-invasive manner through a small percutaneous incision or cannula positioned in an intercostal space in the patient's rib cage. Another problem is that defibrillation of the heart muscles generally requires that the electrodes have a surface area for contacting the heart that is large enough to disperse the high voltage applied to the heart and thereby avoid damage or destruction of the heart cells. Introducing an electrode which is large enough to sufficiently disperse the defibrillation voltage to the heart through the relatively small intercostal spaces in the chest is problematic.

For these and other reasons, improved systems and methods are desired for applying electrical energy to tissue structures in a body cavity via a small percutaneous incision or cannula. Preferably, the systems and methods should be capable of applying an electrical charge to a patient's heart to defibrillate the heart muscle or restart the heart during cardiac procedures in which the heart is arrested or is fibrillating. The system should be configured for introduction through a small percutaneous penetration, such as a cannula positioned in an intercostal space in the patient's chest. The system should also be large enough to contact the heart muscle sufficiently to disperse the high defibrillation voltage and thereby avoid damaging the heart muscle.

SUMMARY OF THE INVENTION

The present invention provides a method and apparatus for thoracoscopic defibrillation of a patient's heart. The method involves introducing a first electrode through an intercostal percutaneous penetration and positioning the first electrode against the heart surface. The term "intercostal percutaneous penetration refers to any penetration, in the form of a small cut, incision, hole, cannula, trocar sleeve or the like, through the chest wall between two adjacent ribs R, which preferably does not require cutting, removing or significantly displacing or retracting the ribs or sternum. A second electrode is placed in contact with the patient's body or directly in contact with the heart. Electrical energy is then delivered through the percutaneous penetration to the first electrode through at least a portion of the patient's heart, and to the second electrode. The electric current applies an electric charge to the patient's heart to defibrillate the heart muscle or restart the heart during, for example, cardiac procedures that involve arresting the heart. The system and method of the present invention are particularly advantageous for thoracoscopic cardiac procedures because the electrical energy is delivered directly through percutaneous penetrations in the patient to electrodes positioned against the heart. This allows the surgeon to artificially restart the heart without opening the patient's chest with a sternotomy and without using external paddles on the chest which pass significantly more current through the patient's body.

In one aspect of the invention, the system comprises an introducer having an elongate shaft with proximal and distal ends and a longitudinal axis therebetween. The introducer includes an electrode coupled to the distal end of the shaft and an electrically conductive element coupled to the electrode and attached to the shaft. The electrically conductive element has a proximal end adapted for coupling the electrode to a source of electrical energy, such as a defibrillation generator, for applying a voltage to the electrode. The electrode is movable between a collapsed position, where the electrode is configured for delivery through an intercostal percutaneous penetration into the thoracic cavity of the patient, and an expanded position, where the electrode defines an electrically conducting surface for contacting the patient's heart.

The electrically conducting surface of the electrode will be large enough in the expanded configuration to apply a voltage to the patient's heart that will defibrillate the heart muscle without causing clinically unacceptable damage or destruction to the heart muscle cells. To that end, the electrode may comprise a substantially flexible material that can be deformed to conform with the patient's heart or the electrode may be pre-shaped to conform to a portion of the heart surface. In addition, the electrode, will have a contact area, in the expanded configuration that is sufficient to disperse the voltage applied to the electrode, thereby reducing the electric current flowing through each heart cell.

The introducer preferably includes a rigid or semi-rigid shaft with at least a distal portion configured for delivery through an intercostal percutaneous penetration. The introducer will include an insulator circumscribing the electrically conducting element between the proximal and distal ends of the shaft to protect surrounding tissue structures from the electric current. The electrically conducting element extends through the rigid shaft from the proximal to distal ends and may be coupled to or integral with the shaft or the shaft itself may be the electrically conducting element. The electrode is preferably at least electrically coupled to the distal end of the electrically conducting element. The electrode may also be mechanically coupled to the electrically conducting element so that both elements can be removed from the shaft once they have been delivered into the thoracic cavity.

The introducer may include an actuator near the proximal end of the shaft for moving the electrode between the collapsed and expanded positions or the electrode may be biased towards the expanded position and held in the collapsed position by the introducer shaft. In one configuration, the electrode is slidably disposed within an inner lumen of the shaft and biased radially outward. When the electrode is moved through the distal end of the shaft, it will automatically expand radially outward into the expanded configuration for positioning against the heart muscle. This configuration allows the surgeon to minimize the profile of the introducer as it passes through the body cavity to decrease interference with other tissue structures within the body cavity.

In a specific configuration, the electrode comprises a plurality of flexible, electrically conductive elements, such as interleaved blades, slidably coupled within an inner lumen of the introducer shaft. The introducer includes a handle attached to the proximal end of the shaft and having an actuator for sliding the blades between a stored position, where the blades are stacked together within the inner lumen, and a deployed position, where the blades extend beyond the distal end of the shaft and are allowed to expand outward to form the conductive surface for defibrillation of the heart. The conductive elements may be configured to expand outward on their own, such as a plurality of flexible conductive filaments or wire, or the shaft may include an actuator for manually expanding the conducting elements.

The second electrode will be positioned so that the electrical energy passes through a suitable portion of the heart to deliver a sufficient electric charge to the heart to repolarize the heart cells or restart the heart muscle. Preferably, the second electrode will be placed against the heart surface at a spaced location from the first electrode, such as the opposite side of the heart. In one embodiment, the second electrode is coupled to the distal end of the introducer. The first and second electrodes are movable between a first position, where they are close together for introduction through the intercostal penetration, and a second position, where they are spaced apart for contacting remote locations on the heart surface and applying a current through the heart between the remote locations. This embodiment reduces the number of required incisions to thereby minimize the trauma to the patient. In another embodiment, the system further includes a second introducer for positioning the second electrode against the heart surface. Similar to the first introducer, the electrode on the second introducer is configured for movement between collapsed and expanded positions so that the electrode can be delivered through an intercostal penetration and suitably positioned against the heart wall.

The invention is particularly useful for defibrillating or restarting contraction of the heart during a cardiac procedure that involves arresting the heart, such as coronary artery bypass grafting, repair and replacement of mitral, aortic, and other heart valves or the like. In this procedure, a cannula is positioned in a percutaneous intercostal penetration on an anterior or lateral side of the patient's chest. A viewing scope, such as a thoracoscope or a direct visualization device, is introduced through another percutaneous intercostal penetration. The heart will be arrested, typically by occluding the patient's aorta between the coronary arteries and the brachycephalic artery with the an expandable balloon and infusing cardioplegic fluid into the coronary arteries. The patient's circulation will be maintained by cardiopulmonary bypass and the thoracoscopic cardiac procedure will be performed. Once this procedure is finished, the expandable balloon is removed from the aorta and infusion of cardioplegic fluid is discontinued to warm the heart muscles. However, the heart muscles may require artificial assistance to resume the normal coordinated contraction or expansion of the ventricles and atrium.

To restart contraction of the patient's heart, the first and second electrodes are collapsed and retracted into the introducer shafts. The electrodes are then guided through percutaneous intercostal penetrations into the thoracic cavity and positioned adjacent the heart. The electrodes are then moved in a distal direction relative to the shaft into the deployed position and extended into the expanded configuration. The electrically conducting surface is positioned against a suitable location on the epicardial surface of the heart or on the pericardium. Of course, the electrodes may be suitably positioned prior to this point during the cardiac procedure. Electrical energy is then delivered through the percutaneous intercostal penetrations to the first and second electrodes such that an electric current flows from the first electrode, through at least a portion of the patient's heart, and to the second electrode. The electric current delivers a charge to the heart muscles to artificially restart the patient's heart.

A further understanding of the nature and advantages of the invention may be realized by reference to the remaining portions of the specification and the drawings.

BRIEF DESCRIPTION OF THE DRAWINGS

FIG. 2A is a transverse cross-sectional view of the cardiac defibrillation device of FIG. 1, illustrating an electrode in a collapsed configuration for introduction through a percutaneous penetration in the patient;

FIG. 2B is a transverse cross-sectional view of the cardiac defibrillation device of FIG. 1, illustrating the electrode in an expanded configuration for applying a defibrillation voltage to the epicardial surface of the patient's heart;

FIGS. 8A–8E illustrate a cardiac defibrillation device incorporating a plurality of interleaved conducting blades;

DESCRIPTION OF THE PREFERRED EMBODIMENTS

Figure 1:
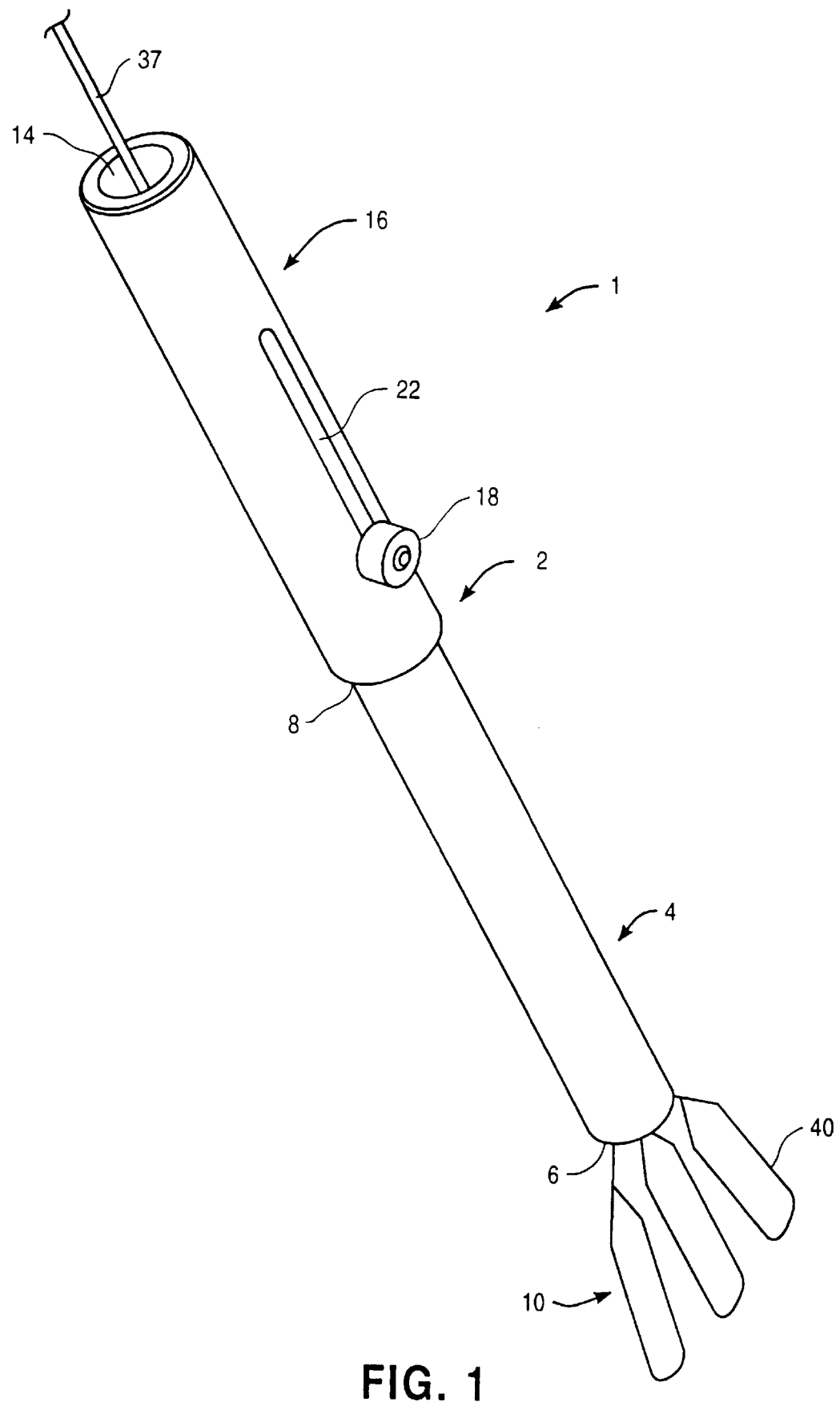
FIG. 1 is a perspective view of a cardiac defibrillation device according to the present invention.

The system and method of the present invention for defibrillating a patient's heart will now be described in detail. Referring to FIG. 1, a cardiac defibrillation device 1 according to the invention includes an introducer 2 having a shaft 4 with a distal end 6, a proximal end 8, and an axial lumen 12 therebetween (see FIGS. 2A and 2B). Shaft 4 is preferably a rigid, metal or plastic tube having an outer diameter in the range of 3–12 mm, usually 5–10 mm, so as to fit within a canula having an internal diameter in the range of 5–15 mm. Shaft 4 can also be introduced directly through a percutaneous incision in the patient. Shaft 4 has a length selected to reach a target site in a body cavity, such as the heart, and to extend sufficiently out of the body cavity to facilitate easy manipulation of introducer 2. Thus, shaft 4 should have a length of 10–40 cm and preferably 15–30 cm. It should be noted that although shaft 4 is shown as having a circular cross-sectional shape in the drawings, shaft 4 could have a rectangular, oval, channel or other cross-sectional shape. Additionally, shaft 4 could be curved or angled.

Referring to FIGS. 2A and 2B, proximal end 8 of shaft 4 is fixed within an axial bore 14 of a handle 16. Handle 16 includes an actuator button 18 with a lower arm 20 projecting into a longitudinal slot 22 of handle 16. Shaft 4 and handle 16 preferably comprise an insulating material, such as a plastic, to protect the surgeon and patient from electric current, as discussed in greater detail below. Lower arm 22 of button 18 is axially movable within longitudinal slot 22 and fixed to an inner tube 24 within axial bore 14 so that tube 24 may slide together with button 18 relative to handle 16 and shaft 4. Cardiac defibrillation device 1 further includes an electrode 10 coupled to tube 24 within shaft 4 of introducer 2 for movement between retracted (FIG. 2A) and deployed (FIG. 2B) positions, as discussed in more detail below.

It should be understood that the invention is not limited to the foregoing configuration. For example, shaft 4 could be axially movable and electrode 10 fixed to handle, or both shaft 4 and electrode 10 could be independently slidable with respect to the handle. In addition, although an actuator in the form of a sliding button has been described in a representative embodiment, various types of actuator mechanisms may be used to slide electrode 10 with respect to handle 16 and shaft 4, including, for example, a plunger mechanism, a pair of scissor-type handles, or a rotatable knob that converts rotational motion into axial motion.

Introducer 2 further includes an electrically conducting element mounted within shaft 4 and connecting electrode 10 with a source of electrical energy. In the representative embodiment, the electrically conducting element comprises a conductive inner tube 28 disposed within outer tube 24 and attached thereto for axial movement with respect to handle 16 and shaft 4. Electrode 10 is attached to a conductive rod 29 fixed to inner tube 28. Inner tube 28 defines a proximal lumen 30 for receiving a connection lead 32 which can be suitably connected to a defibrillation generator 34 (see FIG. 3) for delivering electrical energy to electrode 10. Connection lead 32 comprises a rigid bar 33 fixed to a proximal end 36 of handle 16 via and a flexible lead wire 37 for coupling bar 33 to generator 34. Bar 33 includes a pair of distal contacts 38, 39 extending into proximal lumen 30 of inner tube 28 for electrically connecting inner tube 28 and electrode 10 with generator 34. Distal contacts 38, 39 remain fixed relative to handle 16 and remain in electrical contact with inner tube 28 as electrode 10 slides between the retracted and deployed positions of FIGS. 2A and 2B.

It should be understood that the present invention is not limited to the electrically conductive element described above and illustrated in FIGS. 1, 2A and 2B. For example, the electrically conductive element can be a flexible lead wire extending through axial lumen 12 and attached to inner wall 44 of shaft 4. Alternatively, the shaft 4 itself may comprise an electrically conductive material, such as metal, and include distal mechanical and/or electrical couplings for electrically and mechanically connecting electrode 10 to shaft 4. In this configuration, shaft 4 will include an outer insulating sheath for protecting tissue structures within the patient's body from the electric current. In addition, the sheath will provide a sterile barrier between shaft 4 and tissue structures or body fluids so that introducer 2 can be used with, for example, a number of separate, disposable electrodes.

As best shown in FIG. 2B, electrode 10 comprises a plurality of rigid or semi-rigid, electrically conductive elements or blades 40, which are each connected to conductive rod 29 via conductive beams 42. Beams 42 have proximal portions 43 connected to conductive rod 29 for axial movement therewith. Blades 40 are movable between a collapsed position (FIG. 2A), where the blades 40 are aligned with each other for positioning within inner lumen 12 of shaft 4, and an expanded position (FIG. 2B), where the blades 40 are expanded radially outward from shaft 4 to provide an enlarged surface area for contacting a tissue structure, such as the heart (discussed below). In the preferred configuration, beams 42 are biased outward so as to bias blades 40 outward into the expanded configuration. Thus, when button 18 is positioned in the proximal or retracted position (FIG. 2A), inner walls 44 of lumen 12 hold the beams 42 and blades 40 of electrode 10 in the collapsed configuration. As button 18 is moved in a distal direction with respect to handle 16 and shaft 4, blades 40 and beams 42 are moved beyond the distal end 6 of shaft 2, where beams 42 are released to thereby urge blades 40 radially outward into the expanded configuration (FIG. 2B).

In the expanded configuration, blades 40 define an electrically conducting surface 48 adapted for contacting and conforming to the epicardial surface of the patient's heart. Electrically conducting surface 48 will have a contact area in the expanded configuration that is large enough to disperse the defibrillation voltage over a portion of the heart muscle so that the electric current passing through the heart muscle does not cause clinically unacceptable damage to the heart. The suitable contact area of electrically conductive surface 48 will, of course, vary depending on a number of factors, such as the patient's age, weight, size, etc., the necessary voltage for defibrillating the patient's heart muscle and the like. The Association for the Advancement of Medical Instrumentation has established an American National Standard for minimum performance and safety requirements for cardiac defibrillator devices. In this standard, the minimum contact area/electrode is 9 $cm^2$ for pediatric internal use and 32 $cm^2$ for adult internal use. Thus, the electrically conductive surface 48 of blades 40 in the expanded configuration will usually have a contact area of at least 1 $cm^2$, usually at least 5 $cm^2$, and preferably at least 9 $cm^2$ for pediatric uses, and at least 10 $cm^2$, usually at least 20 $cm^2$ for adult uses, and preferably at least 32 $cm^2$ for adult applications.

Figure 3:
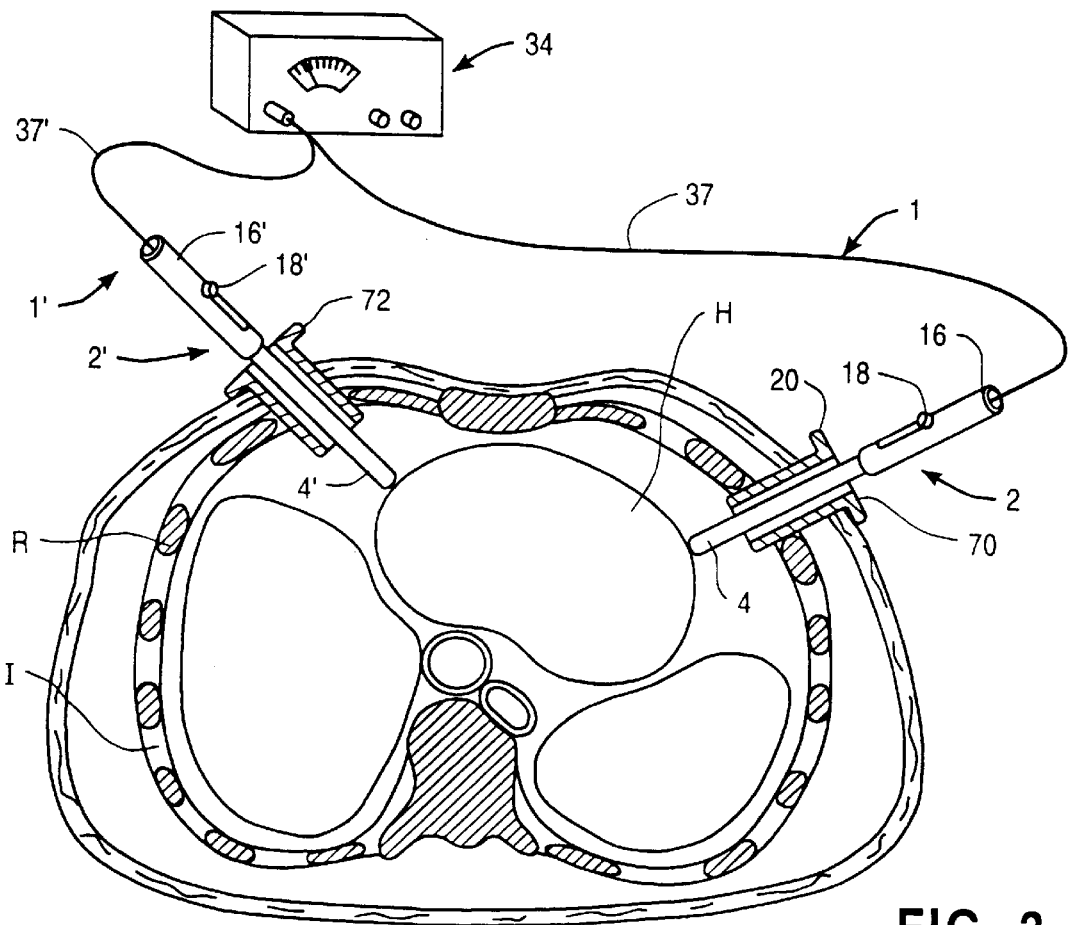
FIG. 3 and 4 are transverse sectional views of the thoracic cavity, illustrating use of a pair of the cardiac defibrillation devices of FIG. 1 for defibrillating the patient's heart.
Figure 4:
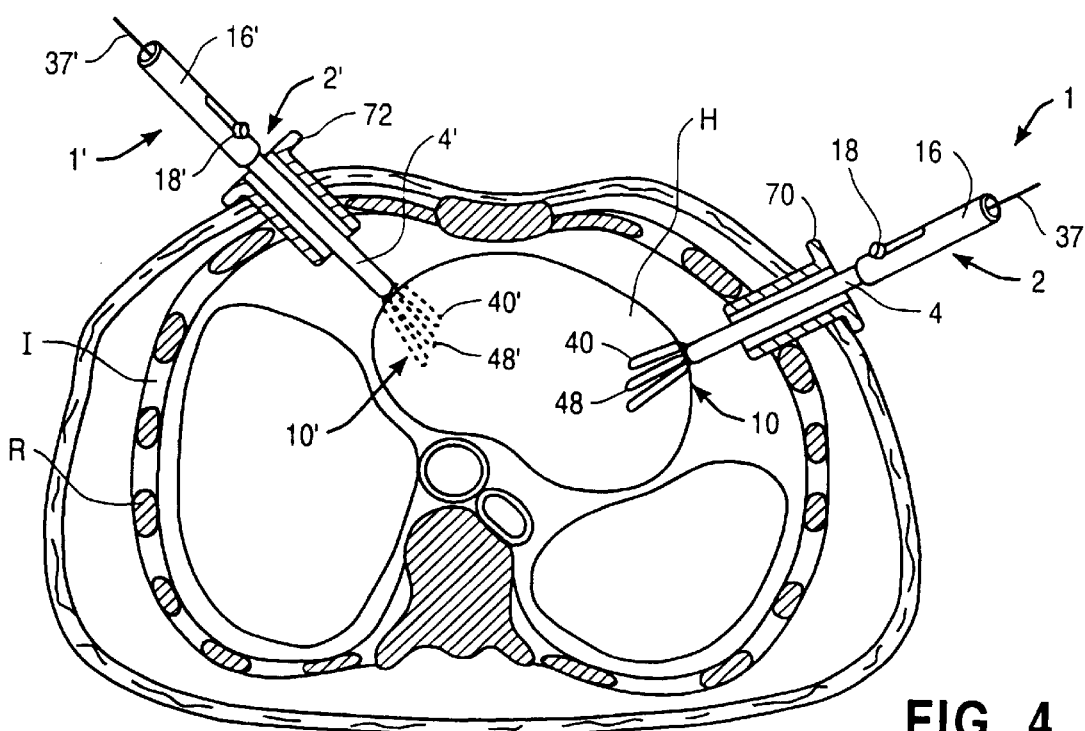

FIGS. 3 and 4 illustrate a method of thoracoscopic defibrillation of a patient's heart according to the present invention. In the representative embodiment, the method of the present invention will be described in the context of restarting a patient's heart that has been arrested for a thoracoscopic cardiac procedure, such as a coronary artery bypass grafting, repair and replacement of mitral, aortic, and other heart valves, repair of atrial and ventricular septal defects, pulmonary thrombectomy, treatment of aneurysms, electrophysiological mapping and ablation of the myocardium and other procedures in which interventional devices are introduced into the chest for intervention on or within the heart or a great vessel.

In this procedure, the patient's heart is arrested by occluding the patient's aorta between the coronary arteries and the brachycephalic artery with an expandable balloon on the distal end of an endovascular catheter introduced via a femoral artery. Cardioplegic fluid is then delivered to the patient's myocardium through a lumen in the same catheter or through a catheter positioned in the coronary sinus via a peripheral vein. Minimally-invasive surgical instruments are then introduced thoracoscopically through trocar sleeves or other access devices in the patient's chest to perform the cardiac procedure on the patient's heart. A more complete description of techniques for performing thoracoscopic cardiac procedures are found in co-pending applications Ser. Nos. 08/281,962 and 08/282,192, now U.S. Pat. Nos. 5,584,803 and commonly assigned, 5,452,733, the complete disclosures of which are incorporated herein by reference.

Figure 18:
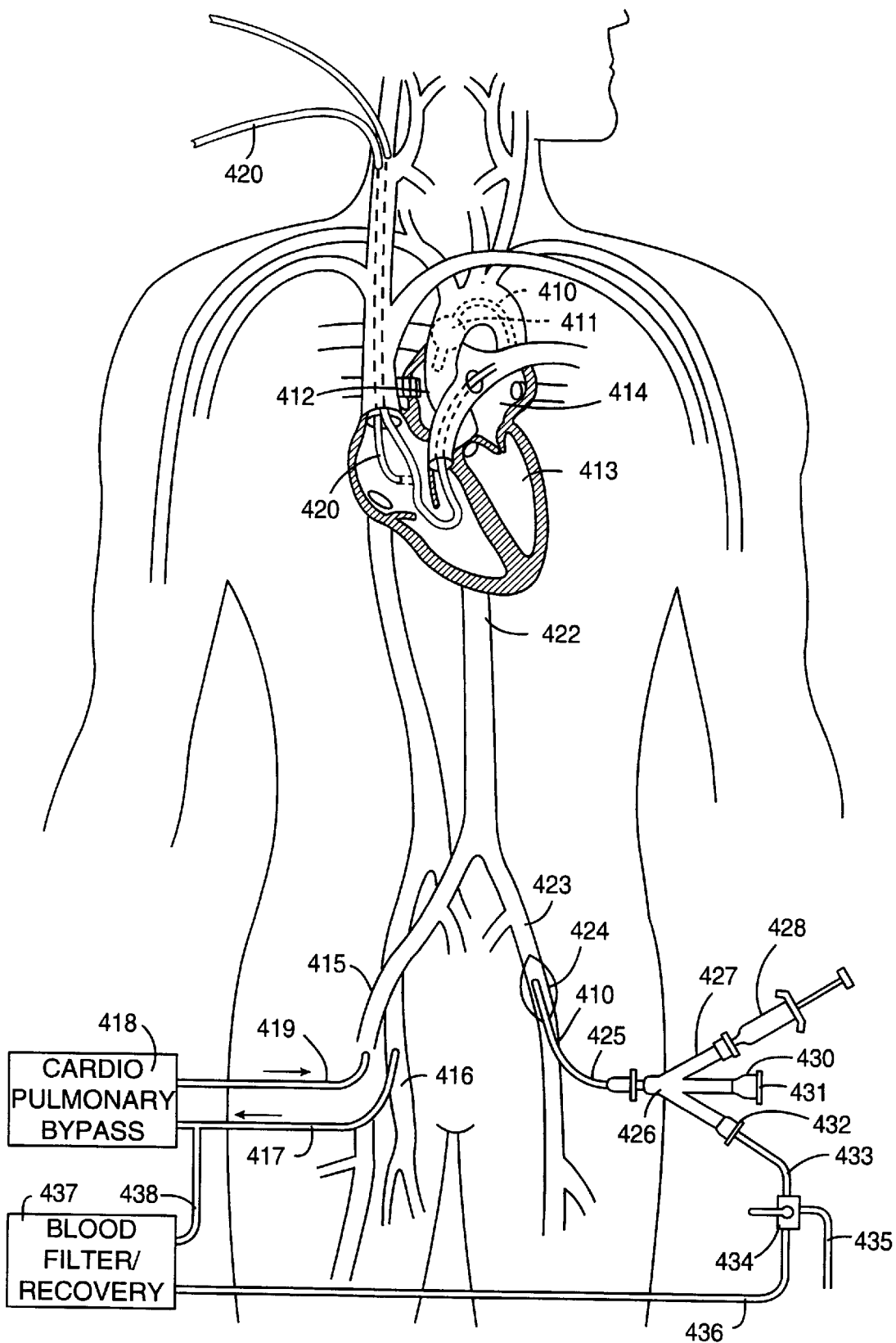

Reference is made to FIG. 18 which schematically illustrates the overall system for arresting the patient's heart for a thoracoscopic procedure. The endovascular procedure system includes an elongated aortic occlusion or delivery catheter 410 which has an expandable member 411 on a distal portion of the catheter which, when inflated as shown, occludes the ascending aorta 412 to separate the left ventricle 413 and upstream portion of the ascending aorta from the rest of the patient's arterial system and securely positions the distal end of the catheter within the ascending aorta. An endovascular device for performing a diagnostic or therapeutic procedure (not shown) may be slidably received within an internal lumen of the aortic occlusion catheter 410. A cardiopulmonary bypass system 418 removes venous blood from the femoral vein 416 through the blood withdrawal catheter 417 as shown, removes $CO_2$ from the blood, oxygenates the blood, and then returns the oxygenated blood to the patient's femoral artery 415 through the return catheter 419 at sufficient pressure so as to flow throughout the patient's arterial system except for the portion blocked by the expanded occluding member 411 on the aortic occluding catheter 410. A fluid containing cardioplegic agents can be delivered through an internal lumen of the endoaortic occluding catheter in an antegrade manner into the aortic root and into the coronary arteries to paralyze the myocardium. Alternatively, a retrograde cardioplegia balloon catheter (not shown) may be placed within the patient's venous system with the distal end of the catheter extending into the coronary sinus to deliver a fluid containing cardioplegic agents to the myocardium in a retrograde manner through the patient's coronary venous system to paralyze the entire myocardium.

The elongated occluding catheter 410 extends through the descending aorta to the left femoral artery 423 and out of the patient through a cut down 424. The proximal extremity 425 of the catheter 410 which extends out of the patient is provided with a multi-arm adapter 426 with one arm 427 adapted to receive an inflation device 428. The adapter 426 is also provided with a second arm 430 with main access port having a hemostasis valve 431 through which the endovascular device is inserted into internal lumen of the aortic occlusion catheter 410. The function of the hemostasis valve 431 may also be provided by a separate adapter which connects to second arm 430 of the multi-arm adapter 426. A third arm 432 connected to bypass line 433 is provided to direct blood, irrigation fluid, and the like to or from the system. A suitable valve 434 is provided to open and close the bypass line 433 and direct the fluid passing through the bypass line to a discharge line 435 or a line 436 to a blood filter and recovery unit 437. A return line 438 may be provided to return any filtered blood, which will be described hereinafter, to the cardiopulmonary bypass system 418 or other blood conservation system.

Figure 19:
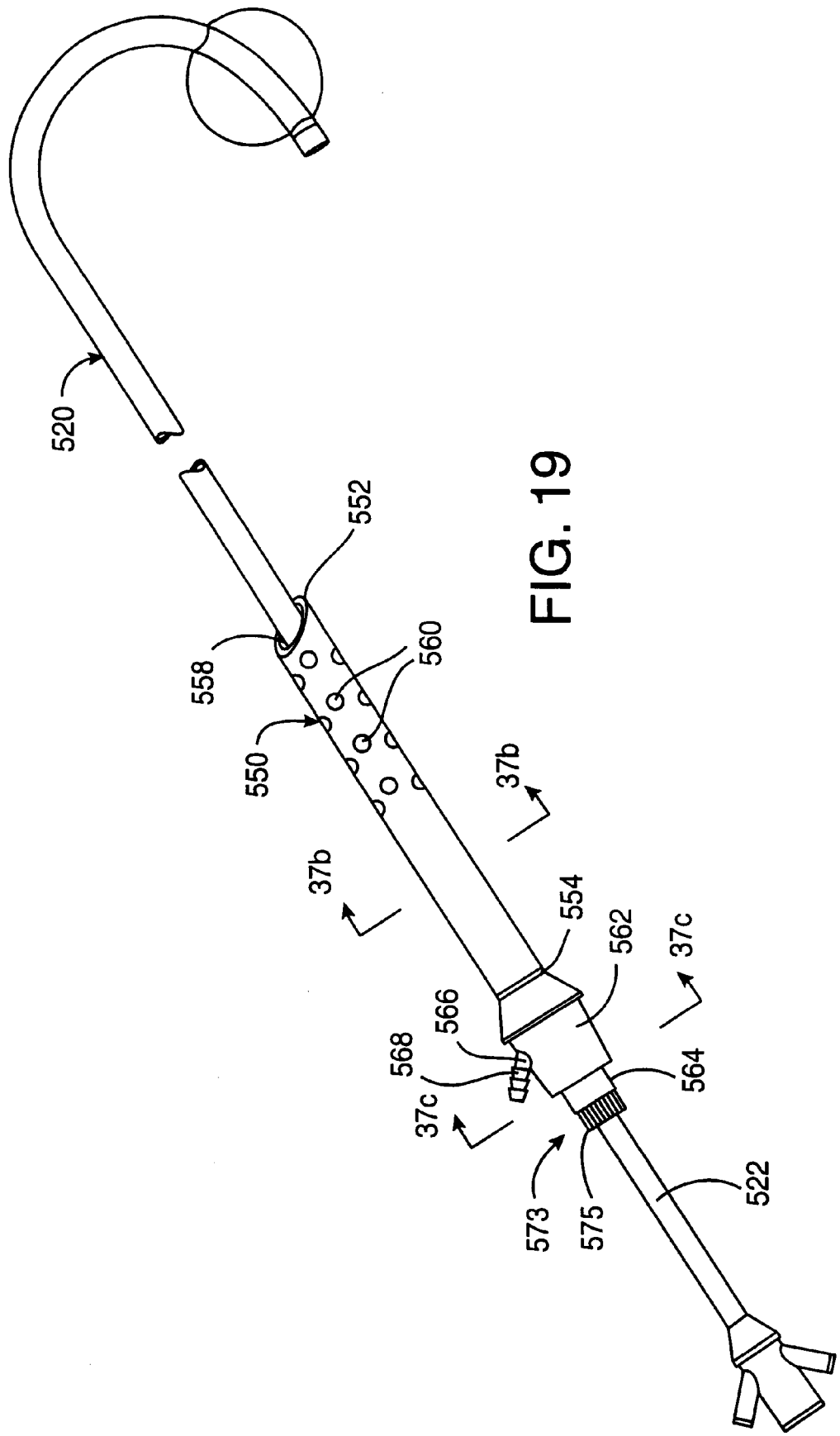
FIG. 19 is a side elevational view of an endovascular partitioning device constructed in accordance with the principles of the present invention.

In a further aspect of the invention, illustrated in FIG. 19, a partitioning device 520 is coupled to an arterial bypass cannula 550 so as to allow both device 520 and cannula 550 to be introduced through the same arterial puncture. Arterial bypass cannula 550 is configured for connection to a cardiopulmonary bypass system for delivering oxygenated blood to the patient's arterial system. Arterial bypass cannula 550 has a distal end 552, a proximal end 554, a blood flow lumen 556 extending between proximal end 554 and distal end 552, and an outflow port 558 at distal end 552. A plurality of additional outflow ports 560 may be provided along the length of arterial bypass cannula 550, particularly near distal end 552. In a preferred embodiment, arterial bypass cannula 550 has a length between about 10 cm and 60 cm, and preferably between about 15 cm and 30 cm.

An adaptor 562 is connected to proximal end 554 of bypass cannula 550, and includes a first access port 564 and a second access port 566, both in fluid communication with blood flow lumen 556. Access port 566 is configured for fluid connection to tubing from a cardiopulmonary bypass system, and preferably has a barbed fitting 568. Access port 564 is configured to receive partitioning device 520 therethrough. Preferably, a hemostasis valve (not shown) is mounted in access port 564 to prevent leakage of blood and other fluids through access port 564 whether or not shaft 522 of partitioning device 520 is positioned therein. The hemostasis valve may have any number of well-known constructions, including, for example, an elastomeric disk having one or more slits through which shaft 522 may be positioned, and a diaphragm adjacent to the disk with a central hole for sealing around the periphery of shaft 522. A hemostasis valve of this type is described in U.S. Pat. No. 4,000,739, which is incorporated herein by reference. Other types of hemostasis valves may also be used, such as duck-bill valves, O-ring seals, and rotational or sliding mechanical valves. In addition, a Touhy-Borst valve 573 including a threaded, rotatable cap 575 may be provided on the proximal end of access port 564 to facilitate clamping and sealing around shaft 522 by tightening cap 575, which compresses O-rings 577 about shaft 522.

Shaft 522 of partitioning device 520 and blood flow lumen 556 of bypass cannula 550 are configured and dimensioned to facilitate sufficient blood flow through blood flow lumen 556 to support full cardiopulmonary bypass with complete cessation of cardiac activity, without an undesirable level of hemolysis. In a preferred embodiment, arterial bypass cannula 550 has an outer diameter of 6 mm to 10 mm, and blood flow lumen 556 has an inner diameter of 5 mm to 9 mm. Shaft 522 of partitioning device 520 has an outer diameter in the range of 2 mm to 5 mm. In this way, blood flow lumen 556, with shaft 522 positioned therein, facilitates a blood flow rate of at least about 4 liters/minute at a pump pressure of less than about 250 mmHg.

After the thoracoscopic procedure has been completed, the patient's heart will be restarted by discontinuing infusion of cardioplegic agents, and removing the aortic clamp from the ascending aorta to allow blood to warm the heart. In some cases, however, the patient's heart does not automatically restart and the surgical team must artificially prompt the heart. To artificially restart the heart according to the method of the present invention, at least one intercostal percutaneous penetration is made in the patient for introduction of cardiac defibrillation device 1. The terms "percutaneous intercostal penetration" and "intercostal penetration" as used herein refer to any penetration, in the form of a small cut, incision, hole or cannula, trocar sleeve, anterior mediastinotomy or the like, through the chest wall between two adjacent ribs R which preferably does not require cutting, removing, or significantly displacing or retracting the ribs or sternum. Usually, the intercostal percutaneous penetration will require a puncture or incision of less than about 6 cm in length and less than about 5 cm in width in a direction generally parallel to the exterior surface of the patient's chest. Introduction of the cardiac defibrillation device could also be made through a more invasive opening, such as a thoracotomy or median sternotomy.

In one configuration, the percutaneous intercostal penetration is an oval port or cannula (not shown) designed to fit between two adjacent ribs R without significantly retracting the ribs. The oval cannula will usually have a width of about 10–30 mm, preferably 15–25 mm, and a height of about 25–75 mm, preferably 30–50 mm. A complete description of a suitable oval cannula for use with the present invention is described in co-pending U.S. application Ser. No. 08/485,600, filed Jun. 7, 1995, the complete disclosure of which is incorporated herein by reference.

It should be noted that insertion of the cannula between the ribs may require a slight retraction of the two adjacent ribs. In addition, a soft tissue retractor may be used in the incision to create an operating window through the intercostal percutaneous penetration for improving the surgeon's view through the incision and for facilitating insertion and removal of thoracoscopic instruments therethrough. Other means of retraction, such as standard surgical retractors, may also be utilized.

A viewing scope 290 (see FIG. 13) is introduced through a trocar sleeve 292 to a position suitable for viewing the heart. The viewing scope can be a conventional laparoscope or thoracoscope, which typically comprise a rigid, elongated tube containing a lens system and an eyepiece or camera mount at the proximal end of the tube. A small video camera is preferably attached to the camera mount and connected to a video monitor to provide a video image of the procedure. Preferably, the scope has a distal end configured to allow lateral or angled viewing relative to the tube. The viewing scope may also have a guidable tip that can be deflected or rotated by manipulating an actuator on a proximal end of the tube. This type of scope is commercially available from Welch Allyn of Skanecteies Falls, N.Y.

As an alternative to the above viewing systems, a visualization system for direct, stereoscopic visualization of the thoracic cavity could be utilized, as described in commonly assigned, co-pending application Ser. No. 08/227,366, filed Apr. 13, 1994, now U.S. Pat. No. 5,888,949 which is incorporated herein by reference. This visualization system comprises a surgical microscope coupled to an access cannula. The access cannula can be positioned percutaneously in an intercostal space, facilitating direct stereoscopic visualization through the access cannula into the chest cavity. This system provides high image quality and the natural hand-eye coordination of direct vision while allowing multiple persons to view the surgical procedure.

As shown in FIG. 3, a cardiac defibrillation system of the present invention preferably comprises a pair of cardiac defibrillation devices 1, 1' each connected to defibrillation generator 34 via flexible wire leads 37, 37'. Defibrillation generator 34 delivers electrical energy to electrodes 10, 10' (FIG. 4) so as to direct a small current of about 3–5 Amps through the heart for a period of approximately 6 milliseconds. A variety of conventional defibrillation generators capable of producing an energy level of at least 5 Joules, which is generally considered the minimum power level for internal defibrillation, may be used in conjunction with the present invention. For example, one suitable defibrillator/monitor is commercially available from Hewlett-Packard, Model M1723A/B, Code Master XL.

As shown in FIG. 3, handles 16, 16' of each introducer 2, 2' are positioned into the retracted position so that electrode blades 40, 40' (not shown in FIG. 3) are collapsed and positioned within each shaft 4, 4' for insertion through access cannulas 70, 72. The distal ends of each shaft 4, 4' are introduced through access cannulas 70, 72, respectively, into the thoracic cavity and positioned near target locations on the epicardial or peridcardial surface of the patient's heart H. The target locations for each electrode 10, 10' will usually be spaced apart from each other on the heart H by a distance of about 1 to 10 cm, preferably 3 to 7 cm. This distance ensures that the defibrillation current will pass through a sufficient portion of the heart so that the electrical charge passing therethrough repolarizes the erratic voltages in the fibrillating heart tissue. Preferably, electrodes 10, 10' will be positioned on opposite sides of the heart to maximize the distance the electric current will flow through the heart, as shown in FIG. 4. The electrodes will preferably remain in the retracted/collapsed configurations until reaching the heart H to provide a smaller profile to minimize contact with tissue structures within the thoracic cavity, such as a graft vessel for a coronary artery bypass procedure.

Referring to FIG. 4, the surgeon now moves each actuator button 18, 18' in the distal direction to slide electrodes 10, 10' distally. When blades 40, 40' pass through the distal ends of each shaft 4, 4', wires 42, 42' (not shown in FIGS. 3 and 4) bias the blades 40, 40' radially outward into the expanded configuration. As discussed above, blades 40, 40' provide an electrically conducting surface 48, 48' with a sufficient contact area to safely apply the high defibrillation voltages to the heart. Blades 40, 40' are then positioned against the target locations of heart H. If necessary, shaft 4 can be rotated to orient blades 40 at a suitable angle to engage heart H. Note that blades 40 are rigid or semi-rigid so that, when the surgeon provides distal pressure against blades 40, the epicardial surface of the heart will conform to the blades to increase the electrical contact therebetween.

Once blades 40, 40' are in position on opposite sides of the heart H, defibrillation generator 34 is activated to apply a defibrillation pulse voltage between electrode blades 40, 40'. The defibrillation voltage generates a small current that flows from electrode blades 40 through the heart H to electrode blades 40' to deliver an electrical charge to the heart muscle to artificially restart the patient's heart.

Once the heart has been restarted, electrode blades 40, 40' of each introducer 2, 2' are disengaged from the patient's heart H. Actuator buttons 18, 18' are then moved in the proximal direction to retract blades 40, 40' within the inner lumen of each shaft 4, 4'. Introducers 2, 2' can then be removed from the patient's body through trocar sleeves 70, 72 to facilitate the surgeon's view during the rest of the operation. Introducers 2, 2' may also remain in the patient's body and can even remain positioned against the heart H to deliver an electrical current when needed. Alternatively, electrodes 10, 10' may be removably attached to introducer shafts 4, 4' so that the electrodes can be removed and adhered to the patient's heart at a suitable point during the operation, e.g., prior to restarting the heart. In this configuration, the electrodes will preferably comprise a suitable mechanical coupling for cooperating with a mechanical coupling on the distal end of shafts 4, 4' and a small lead wire adapted to extend through the percutaneous penetration to electrically couple each electrode with defibrillation generator 34.

Figure 5A:
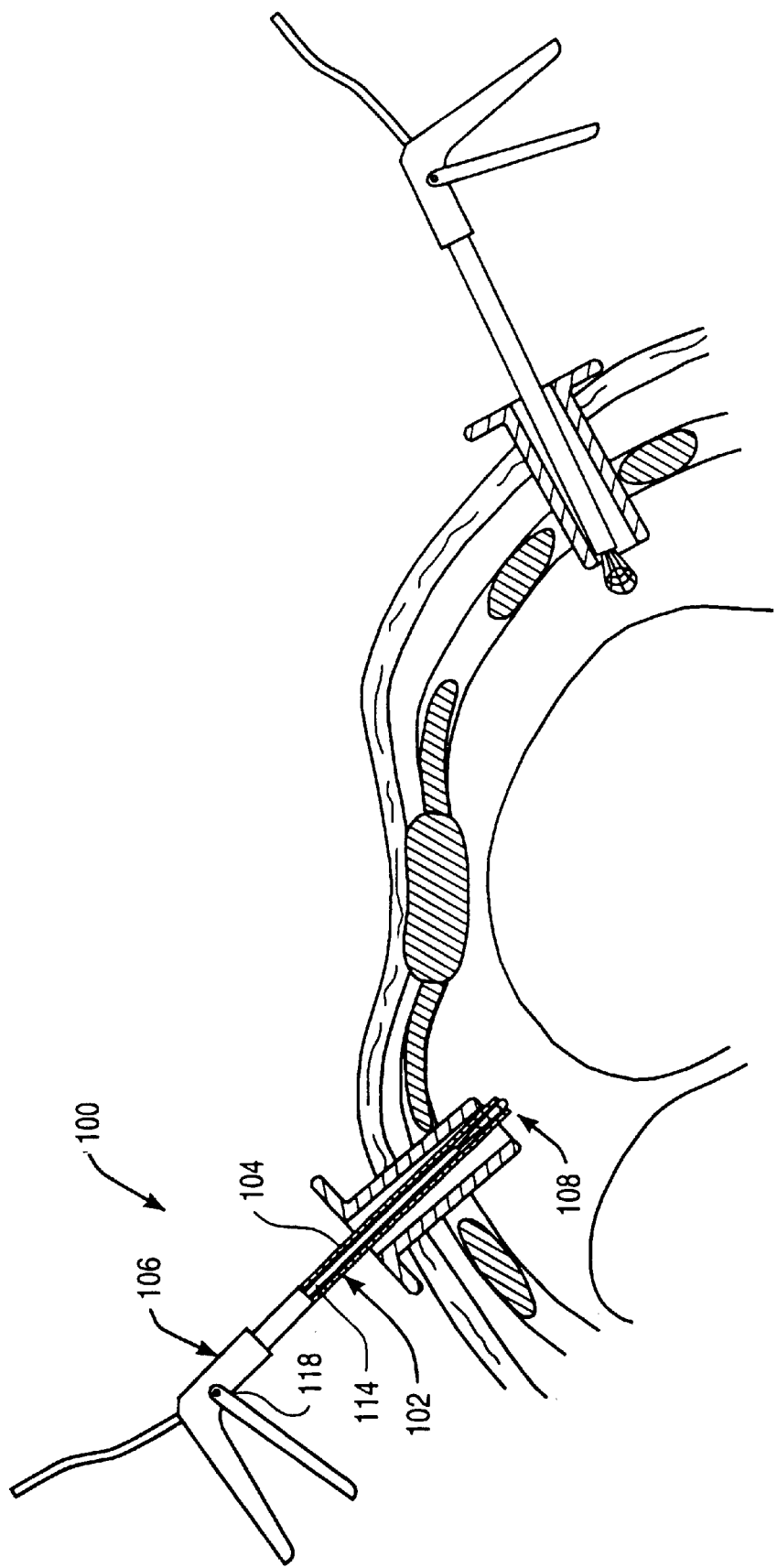
FIGS. 5A and 5B are transverse sectional views of the thoracic cavity, illustrating an alternative cardiac defibrillation device incorporating a flexible electrode member coupled to multiple elements which expand the electrode membrane, 5A illustrating a collapsed configuration and 5B illustrating an expanded configuration.

FIGS. 5A–13 illustrate a variety of alternative embodiments of the present invention. It should be clearly understood that these embodiments are merely representative of the various manners of practicing the present invention and should not be deemed as limiting. FIGS. 5A and 5B illustrate an alternative cardiac defibrillation device 100 comprising an introducer 102 having a shaft 104, a proximal actuator 106 and an electrode 108. Electrode 108 comprises a plurality of fingers 110 coupling a flexible, electrically conductive member, such as a flexible mesh electrode 112, to a rod 114 disposed within an inner lumen (not shown) of shaft 104. Fingers 110 may be electrically conductive or, the device 100 may include a separate wire conductor connecting mesh electrode 112 with an external defibrillation generator (not shown). Proximal actuator 106 includes a handle 118 for axially sliding rod 114 with respect to shaft 104 to move electrode between retracted and deployed positions, as discussed above in the preferred embodiment. In the retracted position, conductive fingers 110 are compressed together and the wire mesh electrode 112 is folded within the wires, as shown in FIG. 5A. In the deployed or expanded configuration, the fingers 110 spread apart to expand the conductive wire mesh electrode 112 and form an enlarged surface for applying a defibrillation voltage to the patient's heart (FIG. 5B).

Preferably, fingers 110 comprise a material having superelastic or shape-memory properties, such as nitinol, that cause the fingers to expand out to preset positions when the fingers are moved past the distal end of the shaft. Mesh electrode 112 is preferably an electrically conductive material, such as a conductive elastomer, foil, wire or mesh conductive cloth or the like. Mesh electrode 112 may also comprise a non-conductive, fluid absorbable material, such as gauze. In this embodiment, the shaft 104 will include an irrigation lumen (not shown) in communication with the gauze for delivering an electrically conductive fluid to the gauze. The electrically conducting fluid saturates the gauze, thereby creating an electrically conducting surface for defibrillation of the heart.

Figure 5B:
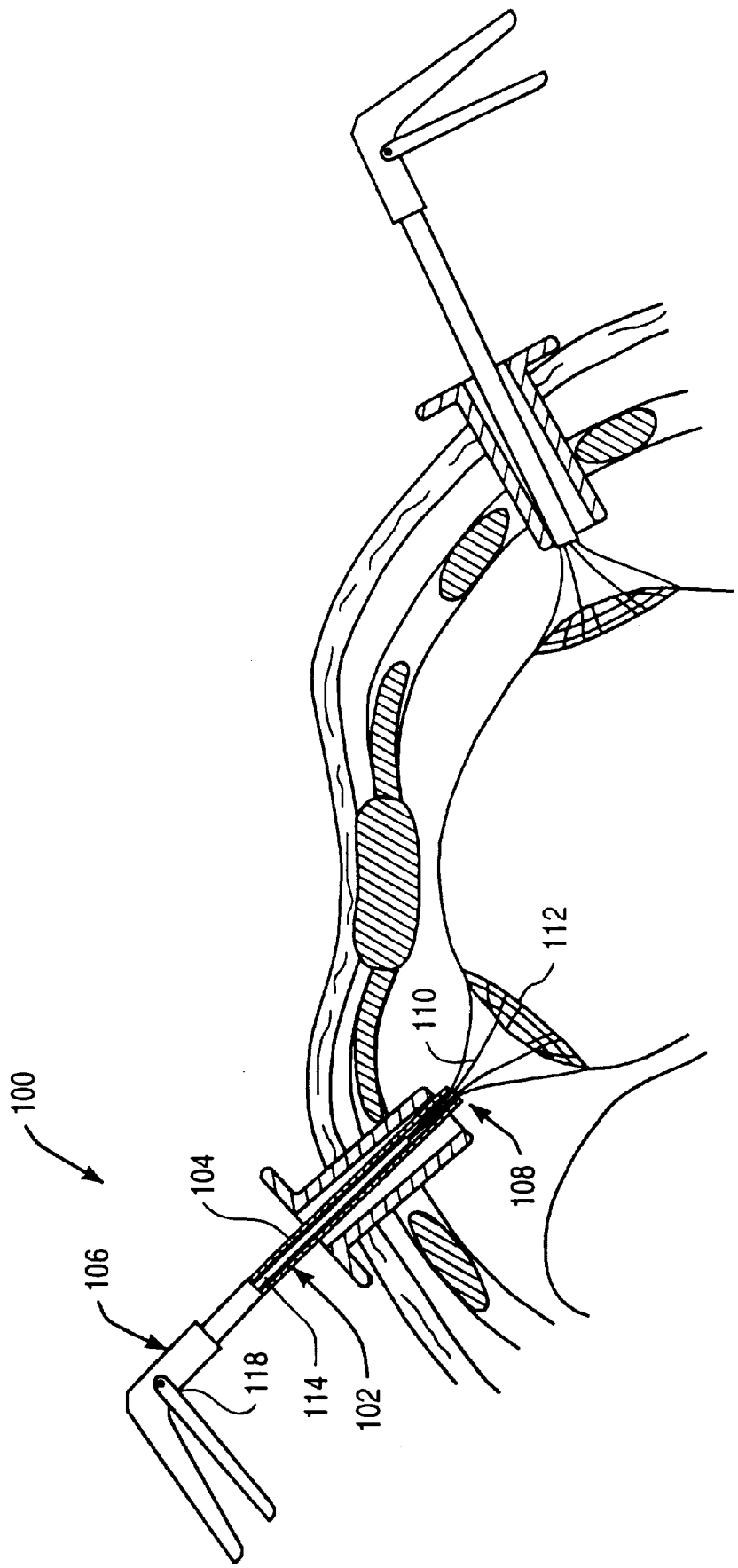

The embodiment of FIGS. 5A and 5B may also comprise a multitude of thin, electrically conducting elements, such as filaments that are separated from each other (i.e., without flexible mesh electrode 112). In this embodiment, the filaments retract into a bundle when the introducer is in the retracted position and expand outward in the deployed position. To generate a suitable conducting surface against the patient's heart, the introducer can be moved distally towards the heart until the filaments deform against the heart surface.

Figure 6A:
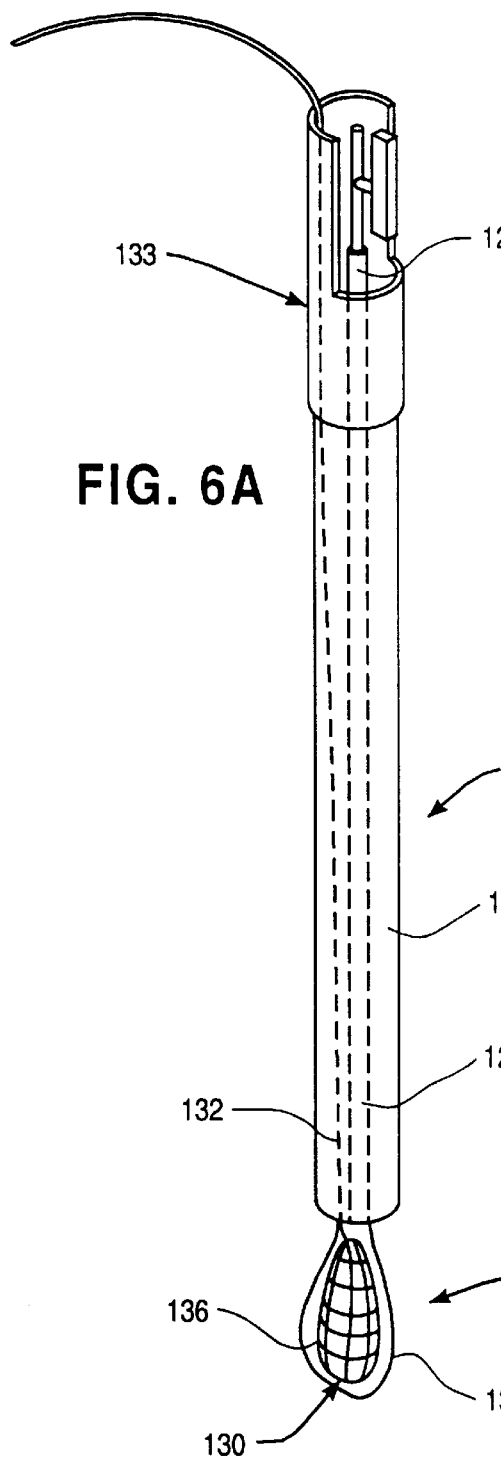
FIGS. 6A and 6B are schematic views of another alternative cardiac defibrillation device incorporating an inflatable balloon with an electrically conductive surface.
Figure 6B:
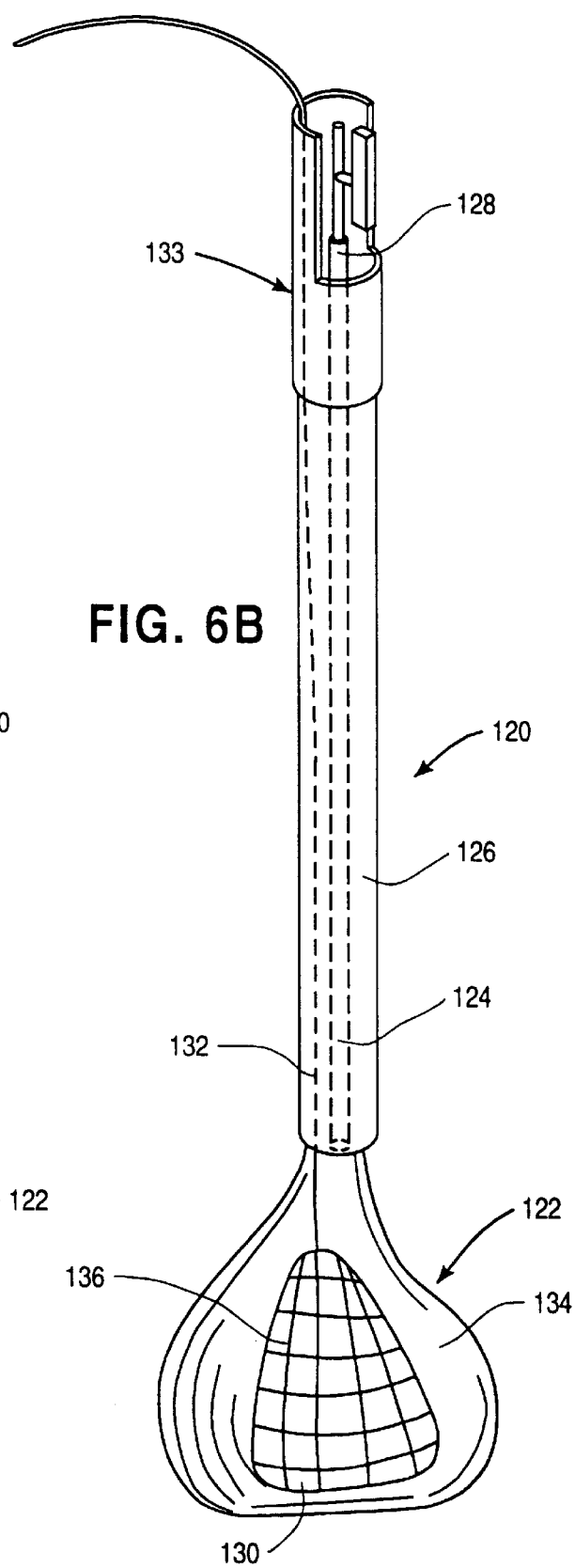

FIGS. 6A and 6B illustrate another cardiac defibrillation device according to the present invention. In this embodiment, an introducer 120 includes an expandable member, such as a balloon 122, attached to the distal end of an inflation lumen 124, which is slidably disposed within the inner lumen of a shaft 126. Inflation lumen 124 has a proximal end 128 connected to a conventional insufflation fitting 133 for coupling to a suitable source of fluid (not shown), which may be a gas, such as air, or a liquid, such as saline, for expanding balloon 122. Balloon 122 will have an electrically conductive portion 130 which is attached to defibrillation generator 34 (FIG. 3) via an inner conductive tube 132 (or other electrically conductive element, such as a wire) extending through shaft 126. In the specific configuration shown in FIGS. 6A and 6B, balloon 122 is manufactured to expand into a spoon or paddle shape which defines an enlarged surface 134 for conforming to the patient's heart. A conductive fabric 136, such as a foil, wire cloth or mesh, conductive elastomer or conductive cloth, is laminated to enlarged surface 134 for applying the defibrillation voltage to the heart.

Instead of laminating a conductive portion to the balloon, the balloon itself may be constructed of an electrically conductive material, such as a heat sealable conductive foil. Alternatively, a front face of the balloon may comprise an electrically conductive material that is adhered to a rear face constructed of, for example, an insulating material to protect other body structures within the thoracic cavity from electric current. The front and rear portions of the balloon can be suitably coupled together via heat sealing or other conventional means. The balloon may have rigid supports, such as axially extending wire elements, to allow pressure on the patient's heart without bending at the proximal end of the balloon.

Preferably, a gas, such as air, will be delivered into the balloon to expand the balloon into its expandable configuration (FIG. 6B). However, other fluids may be used to accomplish this purpose. For example, an incompressible fluid, such as saline, may be delivered into balloon to increase the pressure resistance of the balloon. When the balloon is placed onto the patient's heart, the increased pressure facilitates electrical contact between the electrical conductive portion of the balloon and the patient's heart.

Figure 7:
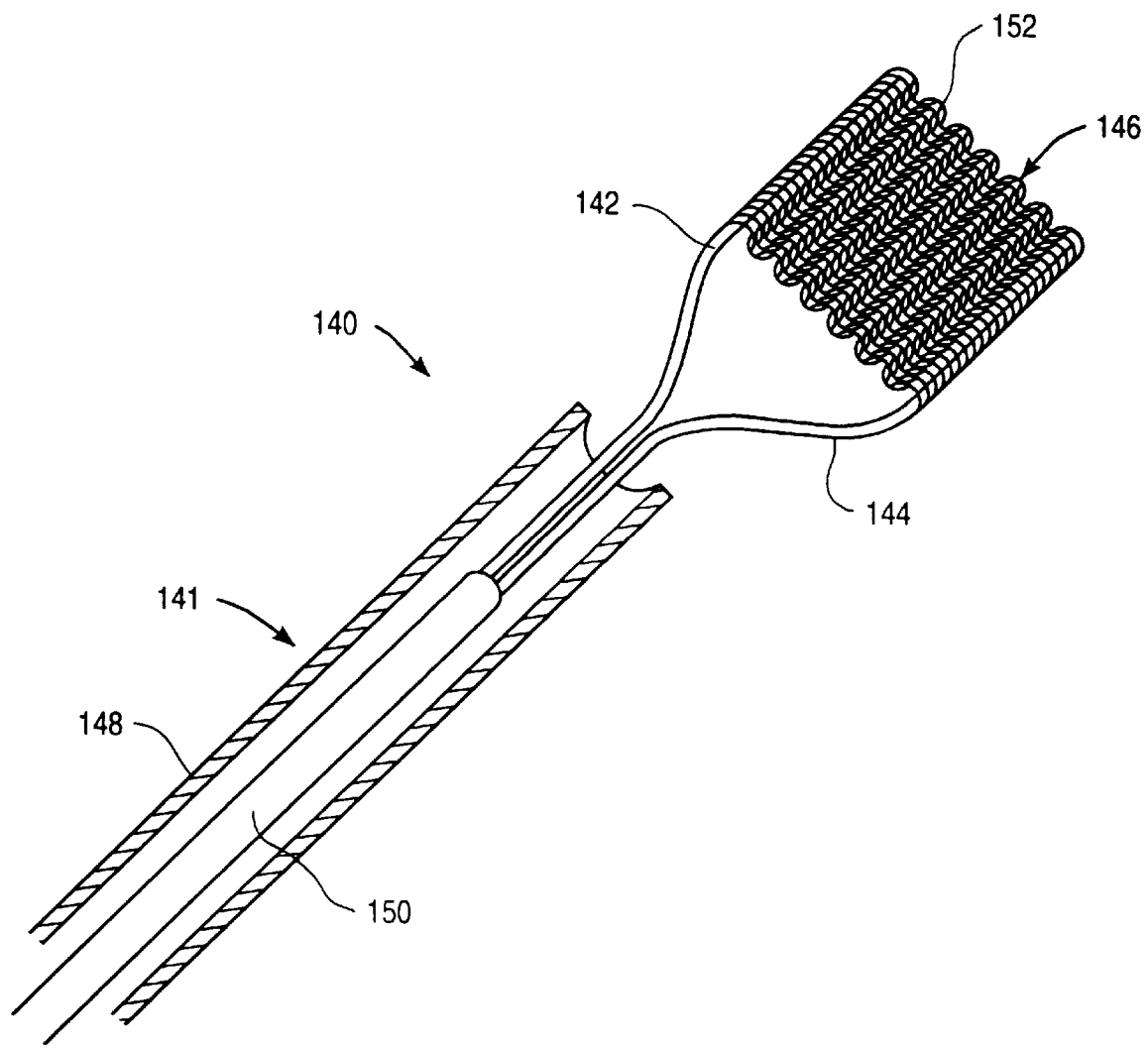
FIG. 7 illustrates a cardiac defibrillation device according to the present invention having a conductive mesh material disposed between expanding wire elements.

FIG. 7 illustrates another cardiac defibrillation device 140 according to the present invention incorporating an introducer 141 having a pair of electrically conductive elongate elements 142, 144, such as metal wire, and a flexible, conductive material 146 connected therebetween, such as wire mesh or cloth, foil, conductive cloth, conductive elastomer or the like. Wire elements 142, 144 may extend proximally through shaft 148 of introducer 141 or they may be suitably coupled to a rod 150 that is slidably disposed within the inner lumen of shaft 148. Retraction of the wire elements 142, 144 within shaft 148 forces them together and causes the flexible, mesh element 146 to collapse so that the introducer can be delivered through an intercostal penetration.

The wire elements 142, 144 are biased away from each other so that, when the rod or wire elements are moved past the distal end of shaft, they move away from each other and stretch the flexible mesh element 146 to form an electrically conducting surface 152 in the expanded configuration. Preferably, the wire elements will generate sufficient tension in the expanded configuration so that pressure can be applied to the surface of the heart with mesh element 146. The wire elements 142, 144 may be biased away from each other in a variety of manners, such as spring force or the like. Alternatively or additionally, wire elements 142, 144 may be formed from resilient materials, such as superelastic/shape memory alloys, e.g., nitinol. Such wire elements will be formed so that they are expanded at room and/or body temperature and are delivered in a constrained and/or unconstrained, cooled condition. Once in position in the thoracic cavity, the wire elements will radially expand due to the resiliency and/or shape memory of their own structure.

FIGS. 8A–8E illustrate a cardiac defibrillation device 160 incorporating a plurality of interleaved conducting blades 162 pivotally mounted to a stationary pivot pin 163 at the distal end of an introducer shaft 164. Blades 162 are movable between a closed position (FIG. 8A), where blades 162 are in stacked relation for insertion through an intercostal penetration, and an open position (FIG. 8B) where the blades 162 are deployed in an interleaved fan configuration. Preferably, blades 162 each include a groove 167 for receiving stationary pivot pin 163 (FIGS. 8D and 8E). Blades 162 are pivotally attached to an inner rod 166 slidably disposed within shaft 164 for rotation about an axis perpendicular to rod 166. As shown in FIG. 8D, as inner rod 166 is moved distally relative to shaft 164, each blade 162 moves distally so that stationary pin 163 slides through groove 167. Grooves 167 are each sized and shaped so that the corresponding blade 162 rotates outward a suitable distance so that all of the blades 162 form the fan configuration shown in FIG. 8B.

A variety of proximal actuators may be used to slide inner rod 166 distally and proximally between the extended (open fan blades 162) and retracted (closed fan blades) positions of FIGS. 8B and 8A. In a specific configuration, shaft 164 includes a handle 168 with a rotatable knob 169 fixed to an outer rod 170 within handle 168. Rod 170 has an inner lumen (not shown) for slidably receiving inner rod 166 and an angled groove 171 for receiving a pin 172 attached to inner rod 166. In the retracted position (FIG. 8A), pin 172 is disposed at the proximal end of groove 171. To move inner rod 166 into the extended position, knob 169 is rotated relative to shaft 164 (usually about 180°), which, in turn, rotates outer rod 170 and forces pin 172 to slide distally along groove 171 to the distal end of groove 171 (FIG. 8B). The distal movement of pin 172 moves inner rod 166 distally into the extended position, thereby rotating blades 162 into the open fan configuration.

As shown in FIG. 8C, interleaved blades 162 have an arcuate transverse cross-sectional shape to substantially conform to the shape of the patient's heart. Blades 162 may comprise an electrically conductive material or they may have a conductive coating on one side 174 for applying voltage to a tissue structure. The conductive portion of blades 162 will be suitably coupled to an electrically conducting element attached to shaft 164 in one of the manners described above. In addition, an insulating sheath coating may cover the opposite side 176 of blades 162 to protect the interior of the patient from the electric current.

Figure 9:
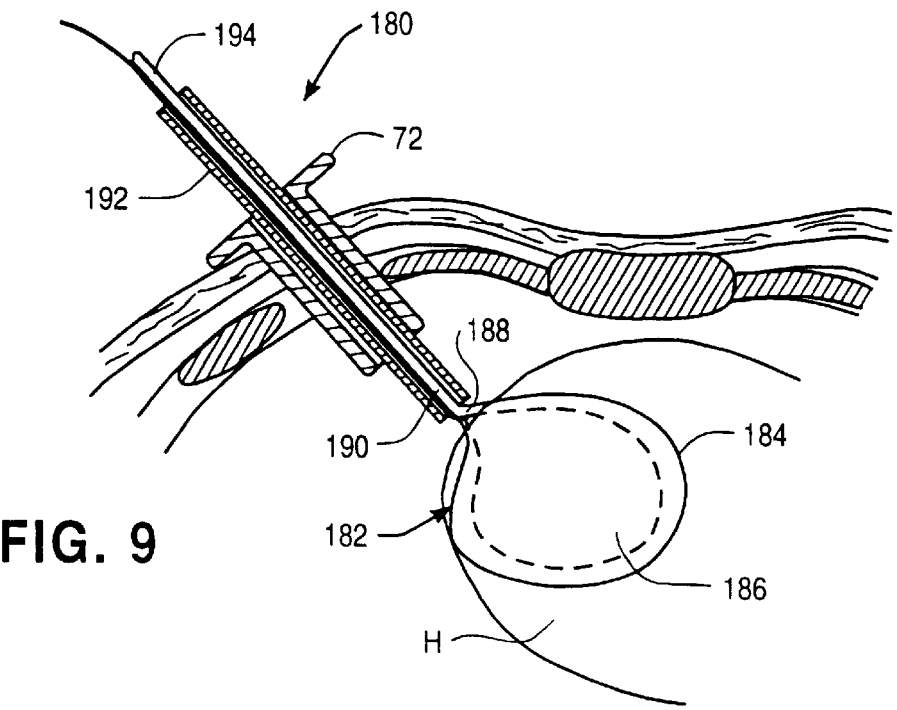
FIG. 9 is a sectional view of the heart illustrating a cardiac defibrillation device that incorporates a suction cup for improving electrical contact between the device and the heart surface.

Referring to FIG. 9, another cardiac defibrillation device 180 according to the present invention incorporates an electrode 182 comprising an elastomeric member 184 having an electrically conducting surface 186, such as foil, mesh, conductive rubber, conductive ink, or other conductive material applied to a distal surface of the elastomeric member 184. Elastomeric member 184 preferably has a low durometer (e.g., 30–50A) and a shape that facilitates compression of the elastomeric member against the surface of the heart. Alternatively, elastomeric member 184 may be preformed to have a radius of curvature similar to the radius of curvature of the heart so that the elastomeric member naturally conforms to the outer surface of the heart. Elastomeric member 184 defines a hole 188 in communication with the distal end of a suction lumen 190 slidably disposed within an introducer shaft 192. Suction lumen 190 has a proximal end 194 coupled to a suitable source of vacuum (not shown) and is axially movable within shaft 192 to retract or deploy the elastomeric member.

In use, elastomeric member 184 is collapsed and proximally retracted within shaft 192 for introduction through an intercostal penetration. Elastomeric member 184 will be constructed of a shape that facilitate collapse into shaft 192, e.g, diamond shaped, conical, dome-shaped or the like. Once positioned within the thoracic cavity, member 184 is distally translated past the distal end of shaft 192 so that it is allowed to naturally expand into the configuration shown in FIG. 9. Elastomeric member 184 is then pressed against the heart so that conductive surface 186 contacts a suitable area of the heart. The vacuum source is energized to draw air through suction lumen 190 and reduce the pressure between elastomeric member 184 and the heart surface, thereby pressing conductive surface 186 against the heart surface. This pressure improves the electrical contact between surface 186 and the heart to increase current flow therebetween.

Figure 10:
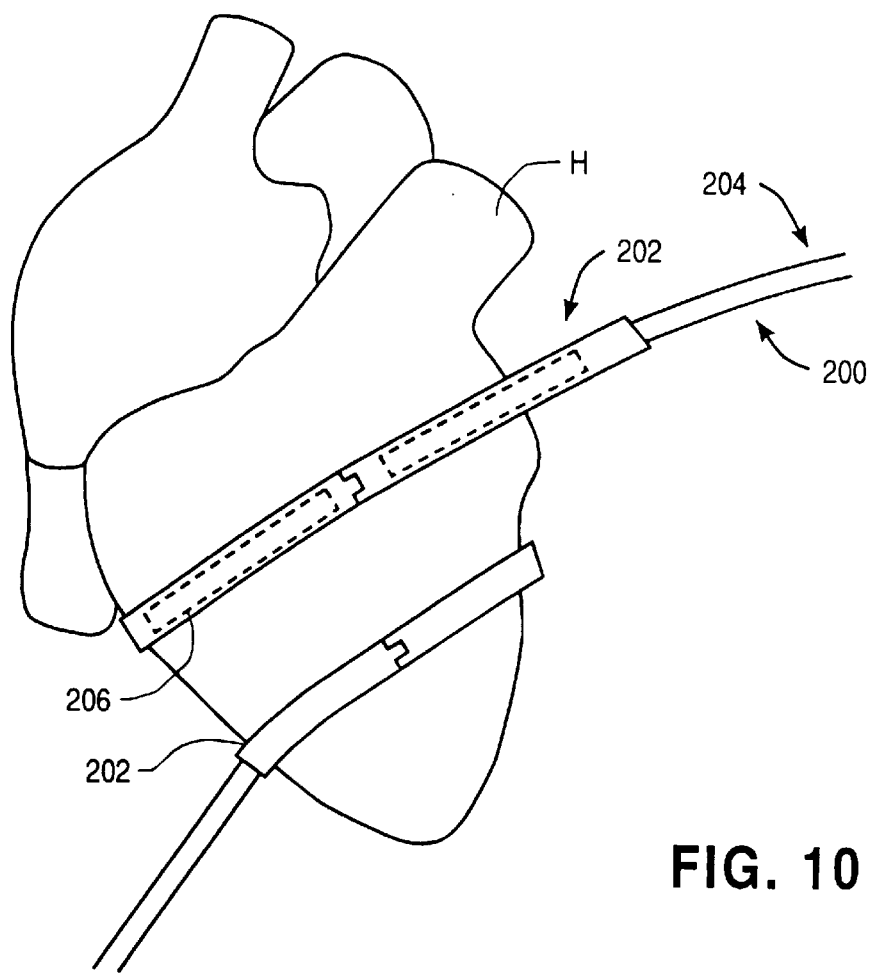
FIG. 10 illustrates a cardiac defibrillation device having a flexible band configured to wrap around a portion of the patient's heart.

FIG. 10 illustrates yet another embodiment of a cardiac defibrillation device 200 incorporating a flexible, elongate band 202 attached to the distal end of an introducer 204. Band 202 has a length suitable for wrapping the band around at least a portion of the patient's heart. Band 202 includes an electrically conducting inner surface 206 for applying a defibrillation voltage to the heart. The conductive surface 206 may be a separate electrode or an electrically conductive coating applied to the inner surface of band 202. Band 202 may be a continuous, flexible element that is deformed around the heart or the band may comprise a plurality of separate elements linked together in a suitable manner. As shown in the FIG. 10, a pair of elongate bands 202, 202' are wrapped around separate portions of the heart H to deliver electrical energy therebetween.

Figure 11:
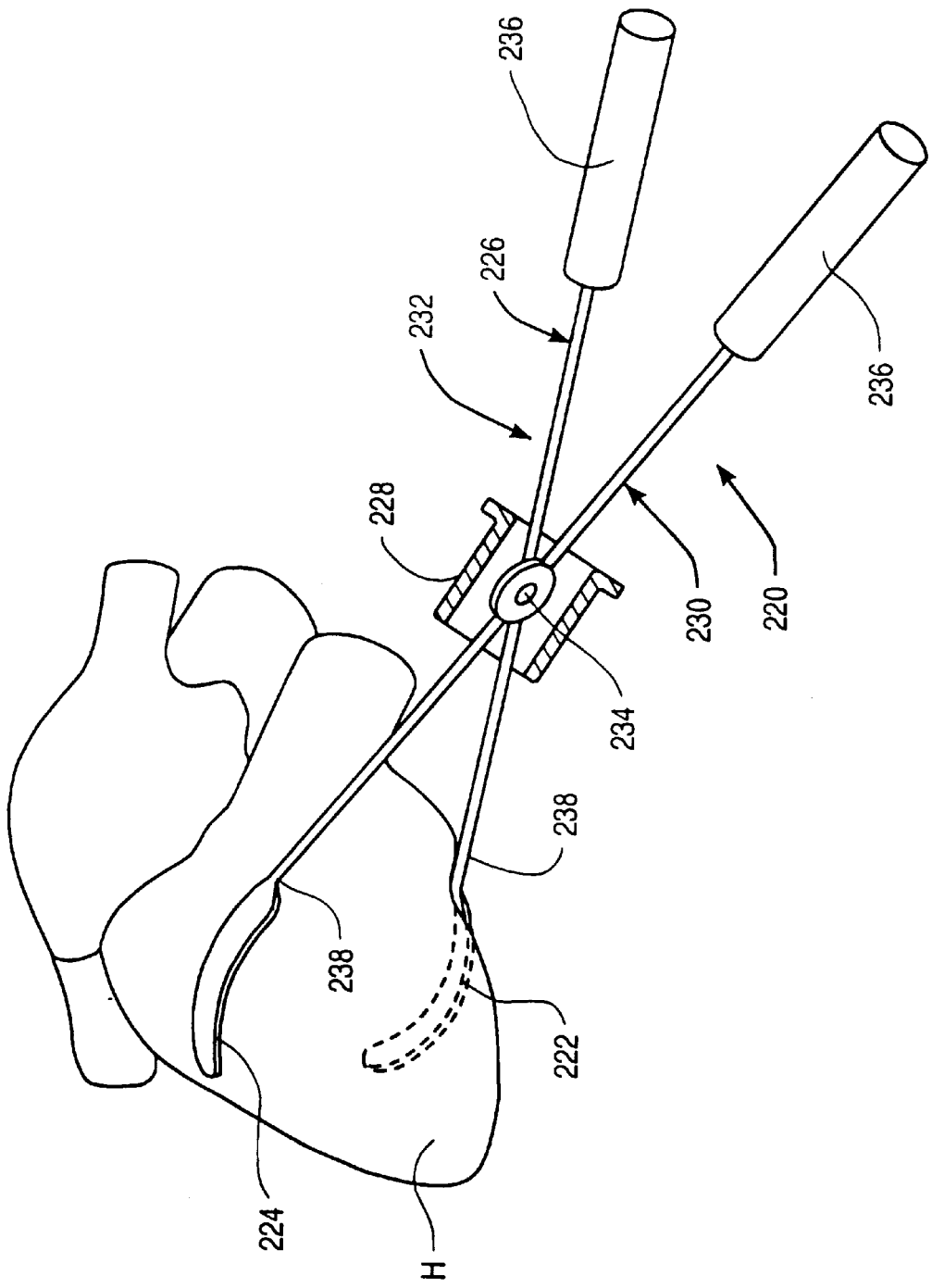
FIG. 11 is a schematic view of a cardiac defibrillation device including a pair of electrodes coupled to a single introducer.

FIG. 11 illustrates a cardiac defibrillation device 220 having first and second electrodes 222, 224 coupled to the distal end of an introducer 226. With this configuration, both electrodes 222, 224 can be delivered through a single trocar sleeve 228 to reduce the number of incisions required in the patient. As shown, introducer 226 includes a pair of elongate shafts 230, 232 pivotally connected together at a pivot 234. Shafts 230, 232 each include a proximal handle 236 and a distal jaw 238. Pivoting handles 236 towards each other will cause jaws 238 to pivot towards each other into a small profile for introduction through trocar sleeve 228. Likewise, rotating handles 236 away from each other causes distal jaws 238 to pivot away from each other into an expanded position.

As shown in FIG. 11, each jaw 238 has an electrode 222, 224 on its inner surface for contacting and applying a defibrillation voltage to the heart. Electrodes 222, 224 are suitably connected to a defibrillation generator via an electrically conductive element (not shown) attached to each shaft 230, 232 such as, for example, lead wires or conductive tubes extending through jaws 238 and handles 236 of each shaft 230, 232. In a specific configuration, the jaws and electrodes have an elongated shape that maximizes the electrically conductive surface area and still allows the jaws and electrodes to pass through an intercostal penetration. Of course, electrodes may also be configured to collapse and expand similar to the electrode configurations discussed above. This embodiment facilitates easier compression of the heart, improving the effectiveness of electrical energy to defibrillate the heart. In addition, this embodiment allows possible single hand use by the surgeon.

Figure 12:
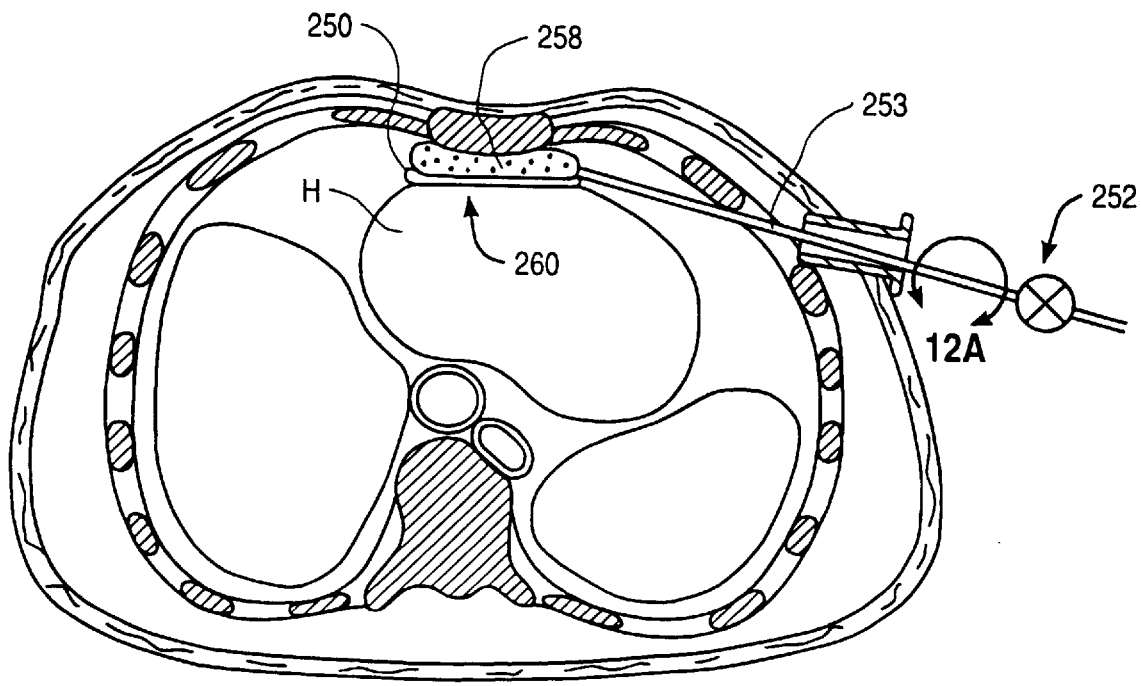
FIG. 12 is a transverse sectional view of the thoracic cavity, illustrating a cardiac defibrillation device and method of inflating a balloon in the thoracic cavity to urge a conductive element against the epicardial surface of the heart.
Figure 12A:
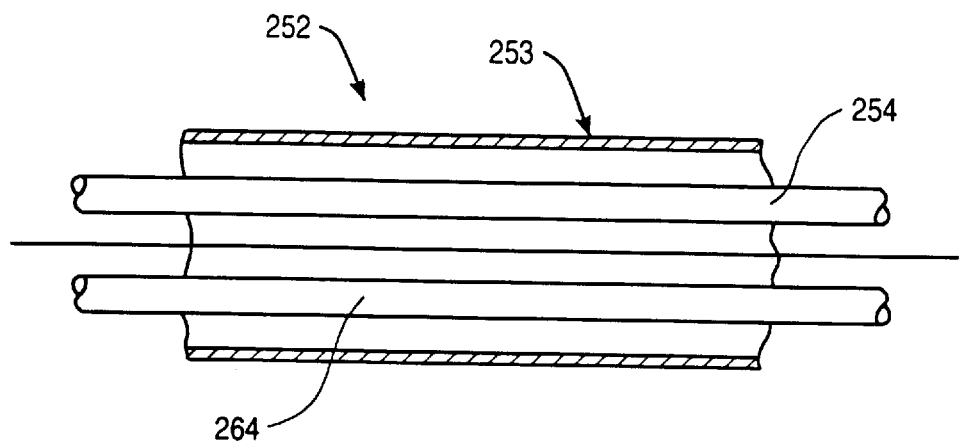
FIG. 12A is a sectional view of an introducer shaft of the defibrillation device of FIG. 12.

Referring to FIGS. 12 and 12A, the present invention includes a method for applying pressure to a thoracoscopic defibrillation electrode 260 to improve the electrical contact between the electrode 260 and the patient's heart H. As shown, an introducer 252 comprises a shaft 253 with an inflation lumen 254 having a distal end in communication with an expandable member, such as a balloon 258, and a proximal end adapted for coupling to a source of fluid (not shown). Introducer 252 will also include a suitable actuator on a proximal handle (not shown) for axially moving balloon 258 and inflation lumen 254 relative to shaft 253 and for delivering inflation fluid through inflation lumen 254 to expand balloon 258.

In the embodiment shown in FIGS. 12 and 12A, electrode 260 is a flexible foam pad 250 configured to retain a suitable volume of an electrically conductive fluid. Introducer shaft 253 further includes a delivery lumen 264 in communication with pad 250 and having a proximal end suitable for coupling to a source of electrically conducting fluid (not shown). Foam pad 250 may be fixed to the exterior of balloon and slidably disposed within shaft 253 for deploying electrode 260, as discussed above. As will be appreciated, the foam pad 250 and balloon 258 can be collapsed to fit within shaft 253, and will automatically expand into a suitable configuration for defibrillating the heart upon deployment past the distal end of shaft 253.

In the inventive method of FIGS. 12 and 12A, foam pad 250 is placed against the heart surface and saturated with electrically conducting liquid. Inflation fluid is delivered through lumen 254 to expand balloon 258 until the balloon exerts, for example, downward pressure against foam pad 260. This pressure will urge pad 250 against the heart to improve the electrical contact between the electrically conducting liquid within pad 250 and the heart surface.

Other configurations for this embodiment are, of course, possible. For example, balloon 258 may be attached to a completely separate introducer shaft that is introduced through a second access canula. Alternatively, the electrode may be detached from its own introducer shaft after being positioned on the heart and the balloon may be reinserted through the same access cannula to urge the electrode against the heart. Alternatively, the electrode could be a conductive foil, mesh or other flexible conductive material.

Figure 13:
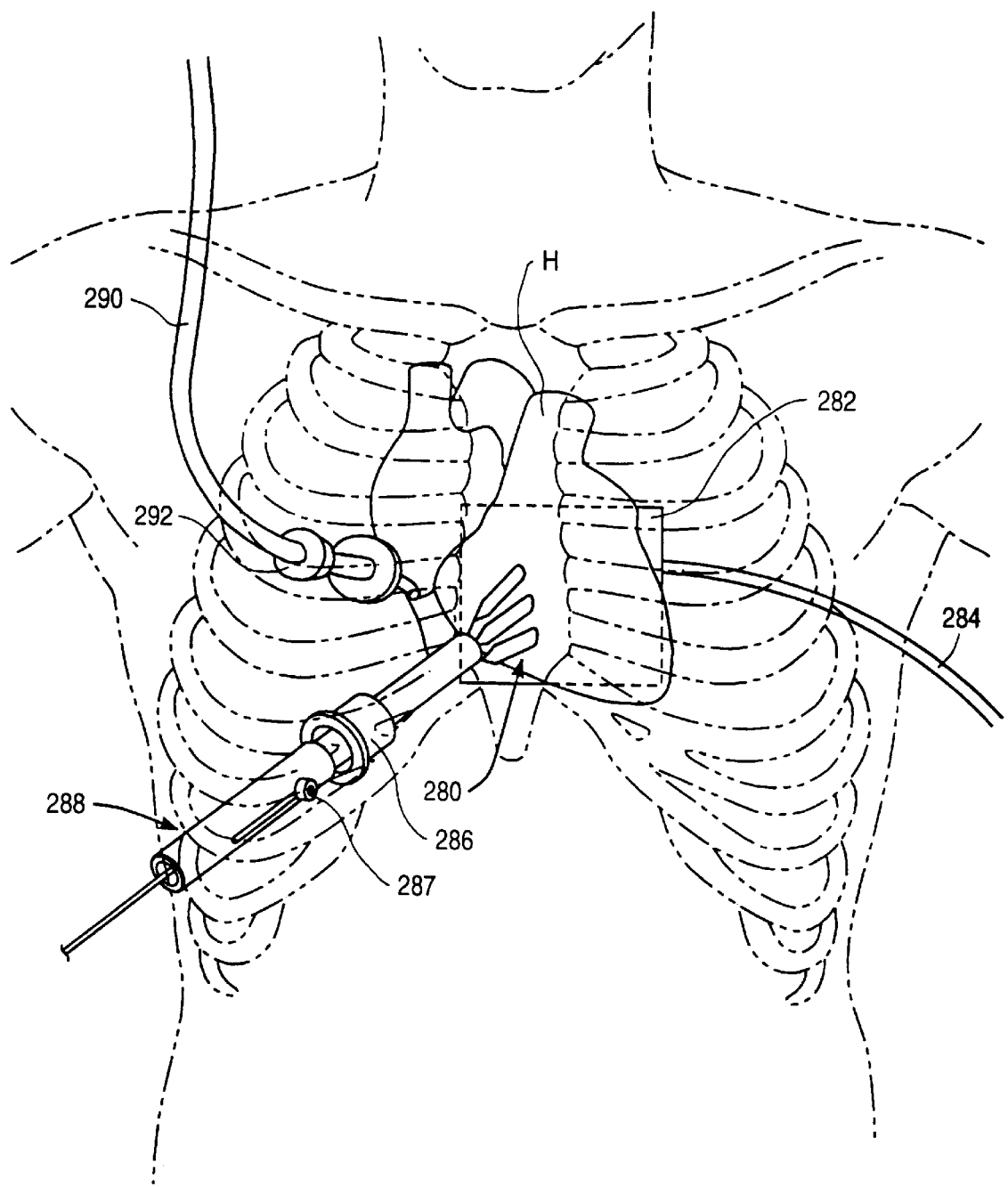
FIG. 13 is a front view of a patient, illustrating another method of cardiac defibrillation which utilizes an external electrode according to the present invention.

FIG. 13 illustrates another alterative method for thoracoscopic defibrillation of the heart according to the present invention. In this method, an electric current is directed along a defined path from an active electrode on the patient's heart, through the patient's body to a return electrode, which is externally attached to a suitable location on the patient. As shown in FIG. 13, a first electrode 280 is thoracoscopically introduced through a trocar sleeve 286 and positioned against the patient's heart H, as described above. A second, external electrode 282 is attached to the patient's outer skin at a suitable location near the heart H, such as along the patient's back, sternum or upper abdomen. Second electrode 282 will preferably comprise a cutaneous patch electrode that is coupled to defibrillation generator (not shown) via an electrode lead wire 284. Second electrode 282 may also comprise other conventional external electrodes, such as a flat paddle having a conducting gelatin applied to a lower conducting surface of the pad to increase the electrical contact with the patient's skin.

A thoracoscope 290 is introduced through a trocar sleeve 292 into a position suitable for viewing the patient's heart. First electrode 280 is deployed against the heart H by manipulating a proximal actuator 287 on an introducer 288, as discussed in detail above and shown in FIGS. 3 and 4. Electrical energy is then delivered through lead wire 284 and an electrically conducting element (not shown) within introducer 288 to electrodes 280, 282. An electric current flows from electrode 280 through the patient's heart, through the patient's body to second electrode 282 on the exterior of the patient's body.

FIGS. 14A–14C and 15 illustrate another embodiment of the cardiac defibrillation device according to the present invention. In this embodiment, defibrillation device 300 comprises an umbrella electrode 302 attached to the distal end of an introducer shaft 304. Umbrella electrode 302 comprises a plurality of support rods 306 (FIG. 15) that extend radially outward to support a flexible, conductive sheet member 308. As shown, electrode 302 is movable between a retracted position (FIG. 14A), where support rods 306 are pressed together and axially aligned for sliding within shaft 304, and an extended position (FIG. 14B), where support rods 306 expand outward similar to an umbrella so that sheet member 308 forms a relatively large, conductive surface 309 for contacting the patient's heart.

Figures 14A, 14B:
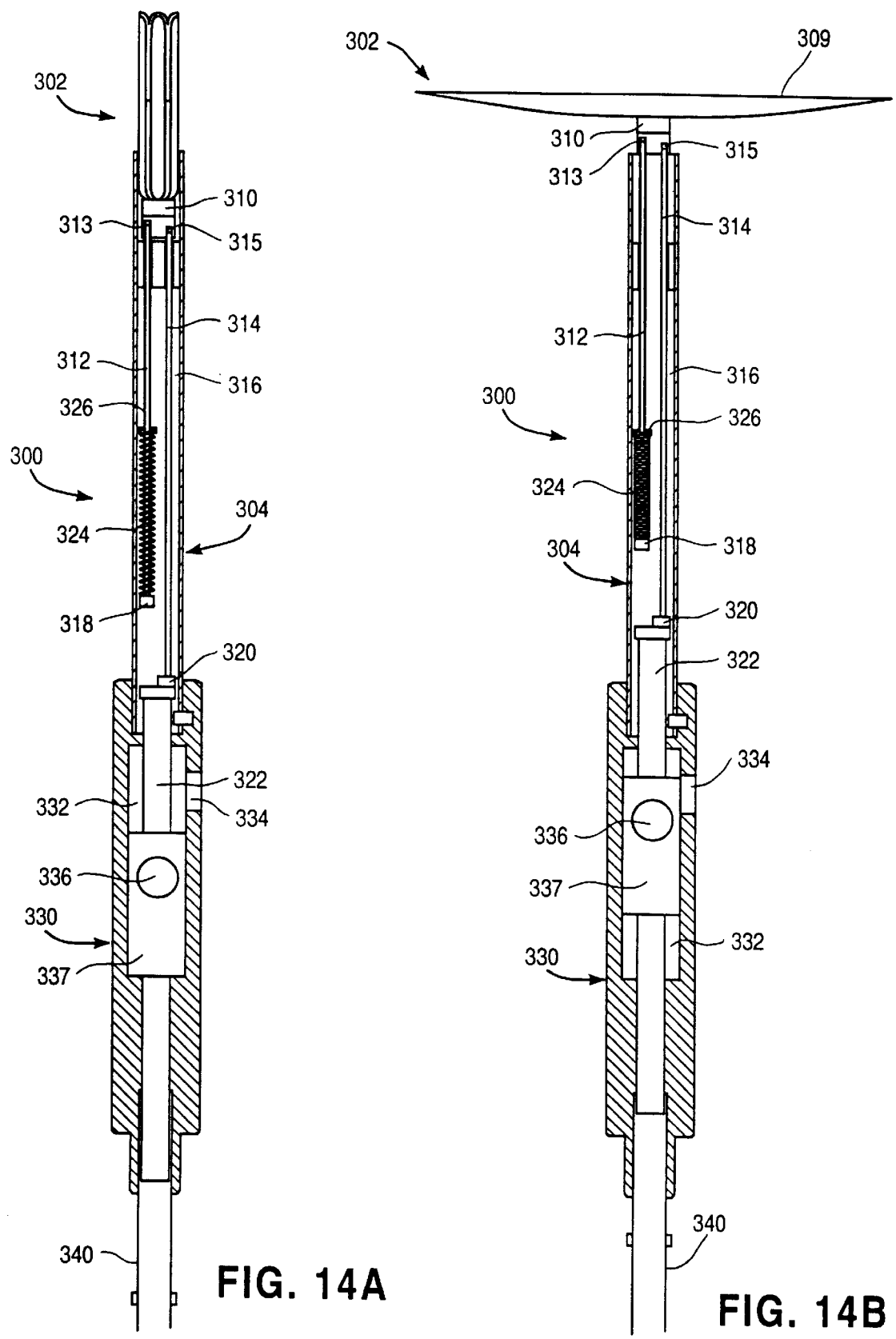
FIGS. 14A–14C are sectional views of a cardiac defibrillation device incorporating an umbrella shaped electrode.
Figures 14C, 15:
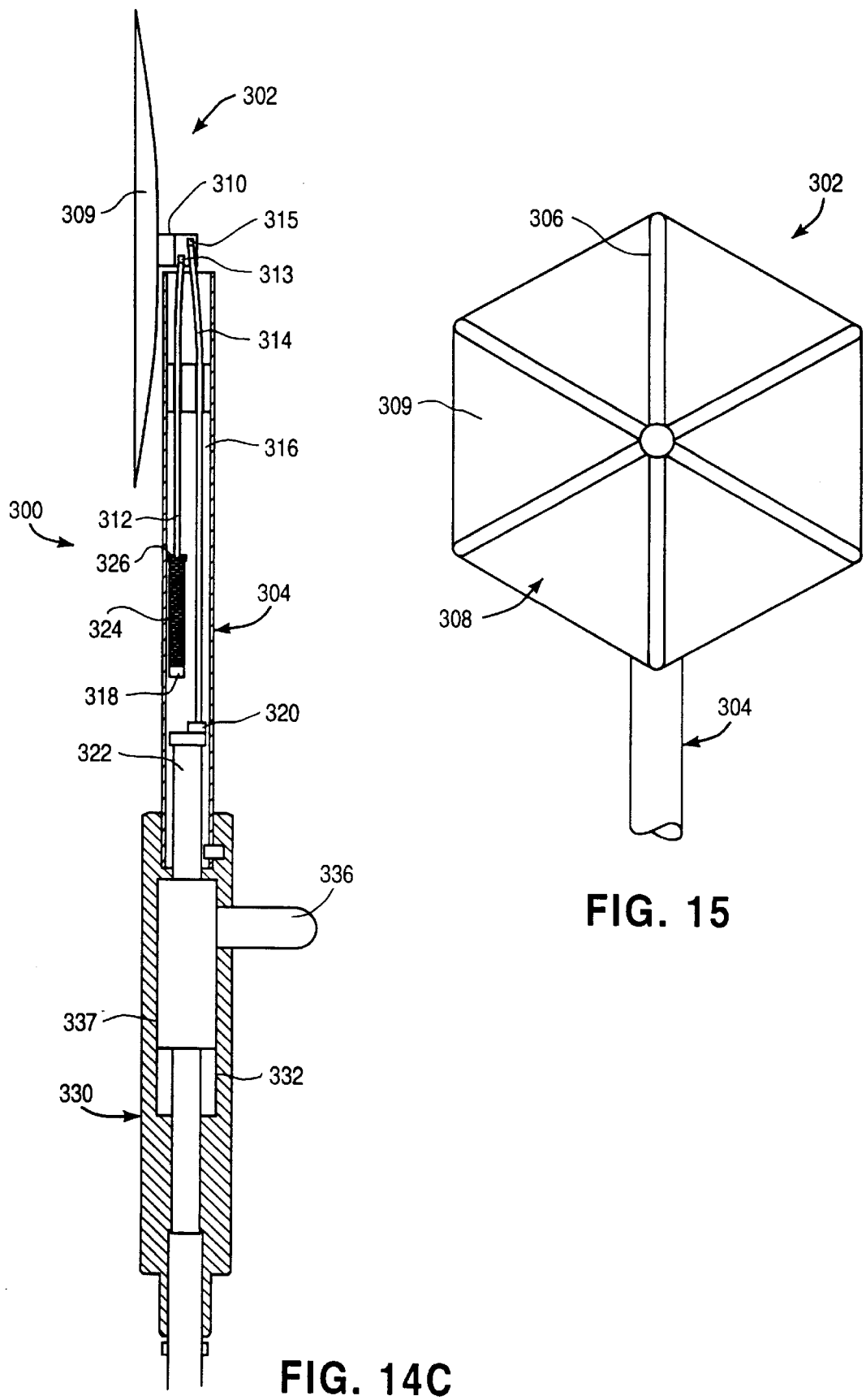
FIG. 15 is a front view of the umbrella shaped electrode of FIGS. 14A–14C.

In a specific configuration, umbrella electrode 302 comprises a central hub 310 pivotally coupled to first and second rods 312, 314 via pivot pins 313, 315, respectively. Rods 312, 314 are slidably disposed within an inner lumen 316 of shaft 304. Rod 314 has a proximal end 320 that abuts against an actuating bar 322 for moving rods 312, 314 and hub 310 axially relative to shaft 304. A spring 324 is positioned between a proximal end 318 of rod 312 and a stop 326 within inner lumen 316 to prevent further distal movement of rod 312. Thus, distal movement of bar 322 causes rods 312, 314 and hub 310 to move distally. As support rods 306 of electrode 302 move past the distal end of shaft 304, they will expand outward into the extended position (FIG. 14B). Further movement of bar 322 in the distal direction causes spring 324 to compress against stop 326 and prevent further movement of rod 312. Rod 314 continues to move in the distal direction, causing hub 310 to pivot about pins 313, 315, thereby rotationally pivoting umbrella electrode 302 about an axis generally orthogonal to the longitudinal axis of shaft 304 (FIG. 14C). Preferably, umbrella electrode 302 is pivotable through an angle of at least about 600, usually at least about 900 relative to shaft 304. This configuration allows the surgeon to pivot electrode 302 to facilitate positioning electrode 302 against the heart.

A variety of proximal actuators may be used to slide actuating bar 322 distally and proximally between the retracted (FIG. 14A), extended (FIG. 14B) and pivoted (FIG. 14C) positions. In a specific configuration, defibrillation device 300 comprises a handle 330 attached to the distal end of shaft 304. Handle 330 has axial and circumferential slots 332, 334 for receiving a knob 336 for axial and circumferential movement through slots 332, 334 relative to handle 330. An outer tube 337 is coupled to knob 336 and disposed within handle 330. Tube 337 has an inner lumen (not shown) for receiving actuating bar 322. Bar 322 is coupled to tube 337 such that bar 322 moves axially with tube 337 as knob 336 is moved through axial slot 332, but tube 337 may rotate freely relative to bar 322 as knob 336 is rotated through circumferential slot 334. The proximal end of bar 322 is suitably coupled to a defibrillation generator connector 340 for delivering electrical energy to electrode 302.

In use, knob 336 is positioned at the proximal end of axial slot 332 in the retracted position of FIG. 14A during introduction through a percutaneous penetration in the patient (not shown). To expand umbrella electrode 302, knob 336 is moved distally through axial slot 332, thereby moving bar 322 and rods 312, 314 therewith. Once knob 336 is moved to a selected axial position along slot 332 between the distal and proximal ends, hub 310 will be disposed beyond the distal end of shaft 304, allowing support rods 306 to expand outward into the umbrella configuration (FIG. 14B). If the surgeon desires to pivot electrode 302, knob 336 is moved to the distal end of slot 332, thereby causing rod 314 to move (while rod 312 is stopped by spring 324 compressing against stop 326) and pivot electrode 302 relative to shaft 304 (FIG. 14C). To lock electrode 302 into the pivoted position of FIG. 14C, the surgeon rotates knob 336 through circumferential slot 334, thereby preventing axial movement of tube 336 and bar 322.

Figure 16A:
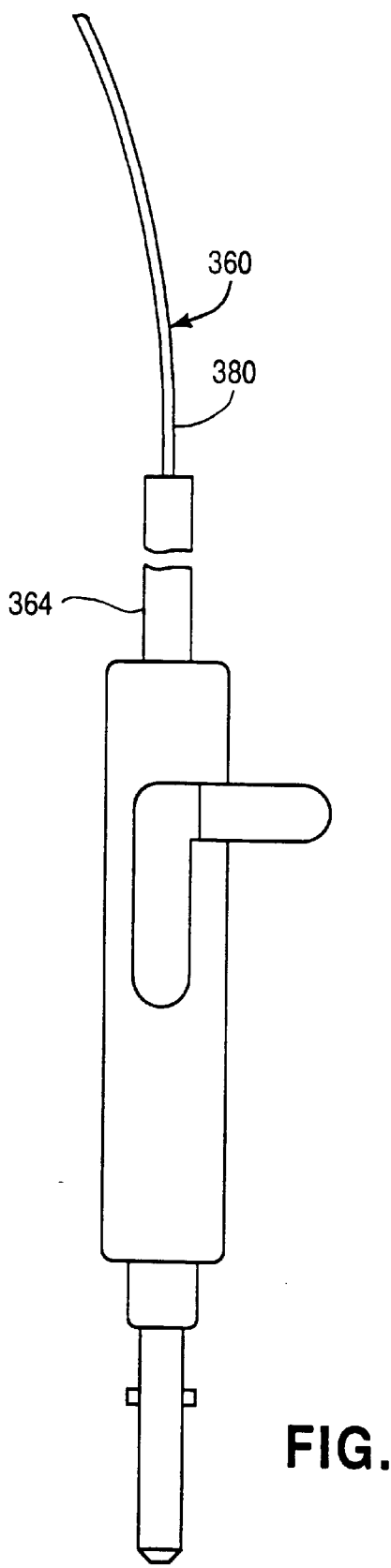
FIGS. 16A and 16B illustrate a cardiac defibrillation device having a pair of support rods supported a flexible electrode member therebetween.
Figure 16B:
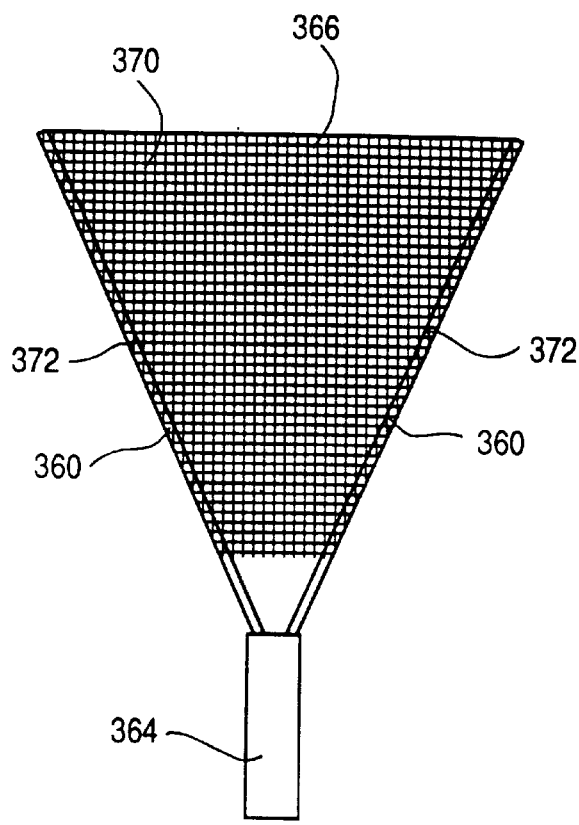
Figure 17A:
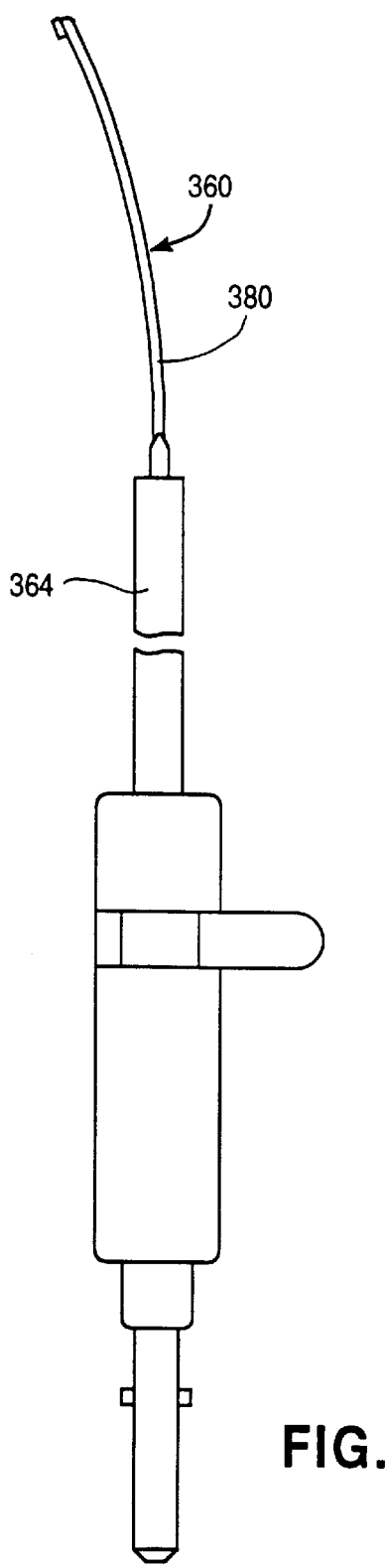
FIGS. 17A and 17B illustrate an alternative embodiment of the device of FIGS. 16A and 16B, FIG. 18 schematically illustrates a representative system for arresting the patient's heart for a thoracoscopic procedure.

FIGS. 16A, 16B, 17A and 17B illustrate another embodiment of the present invention. As shown, this embodiment incorporates a pair of elongate supports 360 attached to an inner rod (not shown) slidably disposed within an introducer shaft 364. A flexible conductive member 366 is attached between supports 360. Member 366 and supports 360 are movable between an extended position (FIGS. 16B and 17B), where supports 360 are moved distal of the distal end of the shaft 364 and expanded radially outward to stretch member 366 into a substantially planar configuration, and a retracted position (not shown), where supports 360 are positioned close to each other and retracted into an inner lumen of shaft 364. As shown in FIGS. 16A and 17A, supports 360 are preferably curved to conform to the surface of the patient's heart. In addition, conductive member 366 may have an insulating coating (not shown) on a rear side of member 366 to protect surrounding tissue structures from the electric current.

Figure 17B:
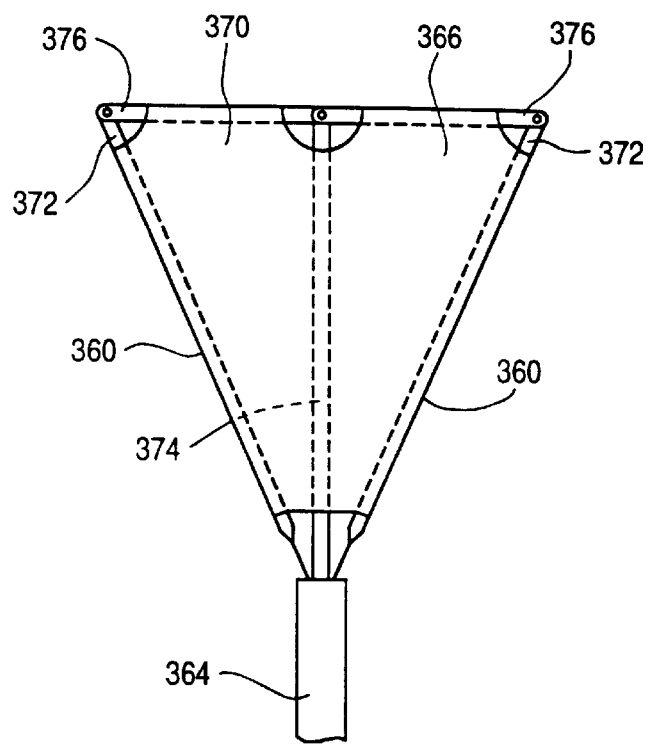

In the embodiment of FIG. 16B, member 366 comprises a metallized mylar or wire mesh 370 attached to a pair of outer metal supports 372. In FIG. 17B, the metallized mylar or wire mesh 370 is wrapped around outer metal supports 372. The electrode in this embodiment further includes a central support bar 374 and a pair of links 376 pivotally coupled to central support bar 374 and outer metal supports 372. Links 376 pivot inward so that outer metal supports 372 pivot towards central support bar 374 in the retracted position.

While the above is a complete description of the preferred embodiments of the invention, various alternatives, modifications and equivalents may be used. For example, in the embodiment of FIGS. 16 and 17, the metal supports may be blades that pivot outward similar to the blades shown in the embodiment of FIG. 8. Therefore, the above description should not be taken as limiting the scope of the invention, which is defined by the appended claims.

What is claimed is:

1. A method for defibrillating a patient's heart comprising:
   contacting a first electrode through a percutaneous penetration against a surface of the patient's heart, the electrode defining an electrically conductive surface having a surface area sufficient for applying a defibrillation voltage to the patient's heart;
   contacting a second electrode against the patient's body;
   delivering electrical energy through the percutaneous penetration between the first electrode and the second electrode such that the electrical energy passes through at least a portion of the patient's heart; and
   removing the first electrode from the patient through a percutaneous penetration.

2. The method of claim 1 wherein the first electrode is attached to a distal end of an introducer shaft, the method further comprising introducing the introducer shaft through a penetration in an intercostal space.

3. The method of claim 2 further comprising detaching the first electrode from the introducer shaft after the introducing step.

4. The method of claim 3 further comprising coupling the first electrode to a source of electrical energy with an electrically conducting element extending through the percutaneous penetration.

5. The method of claim 2 further comprising delivering an electrically conductive fluid through an inner lumen of the introducer shaft to the distal end and saturating a fluid absorbable member at the distal end of the shaft with the electrically conductive fluid.

6. The method of claim 1 further comprising introducing the second electrode through a percutaneous penetration into the thoracic cavity and positioning the second electrode against the patient's heart at a position spaced away from the first electrode.

7. The method of claim 6 wherein the first and second electrodes are attached to a distal end of an introducer shaft, the introducer shaft being positioned through a percutaneous penetration.

8. The method of claim 7 further comprising moving the electrodes from a first position, where the electrodes are close together for delivery through the penetration, to a second position, where the electrodes are spaced apart from each other for positioning at remote locations on the heart surface to apply an electric current from the first electrode, through a portion of the patient's heart, to the second electrode.

9. The method of claim 1 further comprising fastening the first electrode to the epicardial surface of the patient's heart.

10. The method of claim 1 wherein the first and second electrodes are generally positioned on opposite sides of the patient's heart.

11. A method for defibrillating a patient's heart comprising:

delivering a distal portion of an introducer shaft and a first electrode coupled to said distal portion through a percutaneous penetration;

moving the first electrode from a collapsed configuration, where the first electrode is configured for introduction through the percutaneous penetration, to an expanded configuration, where the electrode defines an electrically conductive surface having a surface area sufficient for applying a defibrillation voltage to the patient's heart contacting a second electrode against the patient's body;

delivering electrical energy through the percutaneous penetration between the first electrode and the second electrode such that the electrical energy passes through at least a portion of the patient's heart; and removing at least one of the electrodes after the delivering step.

12. The method of either of claims 1 and 11 wherein the surface area of the electrically conductive surface in the expanded configuration is at least about 9 cm$^2$.

13. The method of claim 11 further comprising moving an actuator at the proximal end of an introducer shaft to move the first electrode into the expanded configuration.

14. The method of claim 11 further comprising biasing the first electrode towards the expanded configuration.

15. The method of claim 11 wherein the electrode is disposed generally in a plane perpendicular to the longitudinal axis of the shaft in the expanded configuration.

16. The method of claim 11 wherein the moving step comprises delivering a fluid through an inflation lumen of an introducer shaft to an expandable member at the distal end of the shaft to expand the expandable member, the electrode being disposed on a portion of the expandable member.

17. The method of claim 11 wherein the moving step comprises sliding a plurality of conducting elements through the distal end of the shaft, the conducting elements extending radially outward into the expanded configuration.

18. The method of claim 11 wherein the first electrode comprises a flexible member having a curved, conductive surface, the step of positioning comprising applying a suction pressure between the flexible member and the heart surface to force the conductive and heart surfaces together.

19. A method for defibrillating a patient's heart comprising:

delivering a first electrode through a percutaneous penetration in the patient;

moving the first electrode to an expanded configuration, where the electrode defines an electrically conductive surface having a surface area sufficient for applying a defibrillation voltage to the patient's heart;

contacting the first electrode against a surface of the patient's heart;

contacting a second electrode against the patient's body; and delivering electrical energy through the percutaneous penetration between the first electrode and the second electrode such that the electrical energy passes through at least a portion of the patient's heart;

wherein the percutaneous penetration is located in the patient's chest area and has a length and a width parallel to an external surface of the patient's chest, the width being less than about 5 cm.

20. A method for defibrillating a patient's heart comprising:

arresting the patient's heart;

introducing a first electrode through a percutaneous penetration in the patient's chest area into the thoracic cavity;

moving the first electrode into an expanded configuration;

positioning the first electrode against a surface of the heart;

positioning a second electrode in contact with the patient's body; and delivering electrical energy through the percutaneous penetration between the first electrode and the second electrode such that the electrical energy passes through at least a portion of the patient's heart.

21. The method of claim 20 further comprising performing a surgical procedure on the patient's heart after the arresting step and before the introducing step.

22. The method of claim 20 wherein the arresting step comprises positioning an occluding member within the ascending aorta to block blood flow therethrough and delivering cardioplegic fluid to the myocardium to paralyze the patient's heart.

23. The method of claim 22 further comprising discontinuing delivery of the cardioplegic fluid and discontinuing occlusion of the ascending aorta prior to applying the defibrillation voltage.

24. The method of claim 20 further comprising viewing an internal portion of the patient's chest through a scope extending through a percutaneous intercostal penetration in the patient's chest during the step of positioning the first electrode.

25. The method of claim 20 wherein the delivering step comprises delivering an electric charge to the heart that is sufficient to restart contraction of the heart.

26. The method of claim 22 wherein the first electrode is attached to a distal end of a rigid introducer shaft, the introducer shaft being delivered through a percutaneous penetration in an intercostal space.

27. A device for defibrillating a patient's heart comprising:
  an elongate shaft having distal and proximal ends and a longitudinal axis therebetween;
  at least one electrode coupled to the distal end of the shaft, the electrode being deployable between a collapsed position, where the electrode is configured for delivery through an intercostal percutaneous penetration into the thoracic cavity of the patient, and an expanded position, where the electrode defines an electrically conductive surface adapted to contact the patient's heart and having a surface area sufficient for applying a defibrillation voltage to the patient's heart; and
  an electrically conducting element integral with the shaft and coupled to the electrode, the electrically conducting element having a proximal end which couples to a source of electrical energy outside of the patient's body for delivering an electrical charge to the electrode.

28. The device of claim 27 further comprising an insulator circumscribing the electrically conducting element between the proximal and distal ends of the shaft.

29. The device of claim 27 wherein the electrically conducting element is a separate element permanently fixed to the shaft.

30. The device of claim 27 wherein the electrically conducting element is a conductive portion of the shaft, the device further comprising an insulating sheath circumscribing at least a distal portion of the shaft.

31. The device of claim 27 wherein the shaft comprises a rigid material.

32. The device of claim 27 further comprising means for grasping the heart tissue to hold the first electrode against the heart surface.

33. The device of claim 27 wherein the electrode comprises an electrically insulating surface opposite the electrically conductive surface for protecting surrounding tissue structures within the body.

34. The device of claim 27 further comprising means for biasing the electrode into the expanded position.

35. The device of claim 27 wherein the electrode comprises a flexible conductive material to facilitate conforming to the heart surface.

36. The device of claim 27 wherein the electrode comprises a substantially rigid material, the conductive surface having an arcuate shape conforming to the heart surface.

37. The device of claim 27 further comprising a second electrode at the distal end of the shaft, the first and second electrodes being movable between a first position, where the electrodes are close together for delivery through the intercostal percutaneous penetration, and a second position, where the electrodes are spaced apart from each other for positioning at spaced-apart locations on the heart surface to apply a defibrillation current from the first electrode, through a portion of the patient's heart, to the second electrode.

38. The device of claim 27 wherein the first electrode has an atraumatic conductive surface.

39. The device of claim 27 wherein the first electrode comprises a flexible expandable member coupled to a plurality of flexible elongate elements, the flexible expandable member being movable between a collapsed position, where the flexible expandable member is collapsed between the elongate elements, and an expanded position, where the elongate elements expand the flexible expandable member to form a electrically conductive surface for contacting the heart surface.

40. The device of claim 39 wherein the flexible expandable member comprises a material selected from the group consisting essentially of electrically conductive wire mesh, conductive elastomer, foil and conductive cloth.

41. The device of claim 27 wherein the first electrode comprises an expandable member, at least a portion of the expandable member comprising an electrically conductive material, the shaft defining an inflation lumen having a distal end in communication an interior of the expandable member and a proximal end adapted for coupling to a source of fluid.

42. The device of claim 27 wherein the first electrode comprises first and second elongate elements and an electrically conductive, flexible material connected therebetween, the elongate elements being biased away from each other.

43. The device of claim 27 wherein the first electrode comprises first and second elongate elements, an electrically conductive, flexible material connected therebetween and an actuator for moving the first and second elongate elements away from each other.

44. The device of claim 43 wherein the elongate elements comprise a superelastic alloy.

45. The device of claim 27 wherein the shaft defines an inner lumen having a proximal end adapted for coupling to a source of vacuum, the first electrode comprising a flexible member having a distal conductive surface, a proximal insulating surface and a hole in communication with the inner lumen of the shaft and with the distal surface for providing a suction pressure between the distal surface and the patient's heart.

46. The device of claim 27 wherein the first electrode comprises a plurality of electrically conductive elongate elements having proximal and distal ends and an inner rod slidably disposed within an inner lumen of the shaft, the proximal ends of the elongate elements being pivotally coupled to the inner rod such that the distal ends are movable between the collapsed configuration, where the distal ends close together, and the expanded configuration, where the distal ends are spread apart.

47. The device of claim 46 further comprising a mechanism for the elongate elements towards the expanded configuration.

48. The device of claim 47 further comprising an actuator for axially moving the inner rod and the elongate elements relative to the shaft.

49. The device of claim 48 wherein the elongate elements comprise a plurality of interleaved movable blades pivotally attached to the distal end of the shaft.

50. The device of claim 48 wherein the elongate elements are support rods, the device further comprising a flexible sheet member attached to the support rods, the support rods and the sheet member forming an umbrella shaped electrode deployable into an open position having a central axis generally parallel to the longitudinal axis of the shaft.

51. The device of claim 50 wherein the umbrella shaped electrode, in the open position, is pivotally coupled to the shaft.

52. A device for defibrillating a patient's heart comprising:
  an elongate shaft having distal and proximal ends and a longitudinal axis therebetween;
  at least one electrode coupled to the distal end of the shaft, the electrode being deployable between a collapsed position, where the electrode is configured for delivery through a percutaneous penetration into the thoracic cavity of the patient, and an expanded position, where the electrode defines an electrically conductive surface adapted to contact the patient's heart and having a surface area sufficient for applying a defibrillation voltage to the patient's heart; and an electrically conducting element attached to the shaft and coupled to the electrode, the electrically conducting element having a proximal end which couples to a source of electrical energy outside of the patient's body for delivering an electrical charge to the electrode;

wherein the surface area of the electrically conductive surface in the expanded configuration is at least about 9 cm$^2$.

53. A device for defibrillating a patient's heart comprising:

an elongate shaft having distal and proximal ends and a longitudinal axis therebetween;

at least one electrode coupled to the distal end of the shaft, the electrode having an electrically conductive surface area sufficient for applying a defibrillation voltage to the patient's heart; and an electrically conducting element attached to the shaft and coupled to the electrode, the electrically conducting element having a proximal end which couples to a source of electrical energy outside of the patient's body for delivering an electrical charge to the electrode;

wherein the electrode is removably coupled to the distal end of the shaft.

54. The device of claim 53 wherein the distal end of the shaft includes a mechanical coupling for attaching and detaching the electrode to the shaft, the shaft further including an electrical coupling at the distal end of the shaft for electrically communicating the electrode with the electrically conducting element.

55. The device of claim 27 or claim 52 wherein the surface area of the electrically conductive surface in the expanded configuration is at least about 32 cm$^2$.

56. A device for defibrillating a patient's heart comprising:

an elongate shaft having distal and proximal ends and a longitudinal axis therebetween;

at least one electrode coupled to the distal end of the shaft, the electrode being deployable between a collapsed position, where the electrode is configured for delivery through a percutaneous penetration into the thoracic cavity of the patient, and an expanded position, where the electrode defines an electrically conductive surface adapted to contact the patient's heart and having a surface area sufficient for applying a defibrillation voltage to the patient's heart; and an electrically conducting element attached to the shaft and coupled to the electrode, the electrically conducting element having an electrically conducting surface and a proximal end which couples to a source of electrical energy outside of the patient's body for delivering an electrical charge to the electrode;

wherein the shaft and electrode are configured to pass through a percutaneous penetration having a width parallel to an external surface of the chest of less than about 5 cm, and wherein the electrode comprises an electrically insulating surface opposite the electrically conducting surface for protecting surrounding tissue structures within the body.

57. A device for defibrillating a patient's heart comprising:

an elongate shaft having distal and proximal ends and a longitudinal axis therebetween;

at least one electrode coupled to the distal end of the shaft, the electrode having an electrically conductive surface area sufficient for applying a defibrillation voltage to the patient's heart; and an electrically conducting element attached to the shaft and coupled to the electrode, the electrically conducting element having a proximal end which couples to a source of electrical energy outside of the patient's body for delivering an electrical charge to the electrode;

wherein the shaft includes an actuator at the proximal end for moving the electrode into the expanded position;

wherein the electrode comprises a material capable of absorbing an electrically conducting fluid, and the shaft defines a delivery lumen and the electrode defines an inlet in communication with the delivery lumen for receiving the electrically conducting fluid.

58. A device for defibrillating a patient's heart comprising:

an elongate shaft having distal and proximal ends and a longitudinal axis therebetween;

at least one electrode non-removably coupled to the distal end of the shaft, the electrode being movable between a collapsed position, where the electrode is configured for delivery through an intercostal percutaneous penetration into the thoracic cavity of the patient, and an expanded position, where the electrode defines an electrically conductive surface adapted to contact the patient's heart and having a surface area sufficient for applying a defibrillation voltage to the patient's heart; and an electrically conducting element coupled to the electrode and having a proximal end adapted for coupling to a source of electrical energy outside of the patient's body for delivering electrical energy to the electrode.

59. The device of claim 58 wherein the shaft comprises a rigid material.

60. A cardiac defibrillation system for defibrillating a patient's heart, the system comprising:

a defibrillation generator for applying a defibrillation voltage including a conductor for connection to an external power source;

a first electrode movable between a collapsed position, where the electrode is configured for delivery through an intercostal penetration into the thoracic cavity of the patient, and an expanded position, where the electrode defines an electrically conductive surface adapted to contact the patient's heart and having a surface area of at least 9 cm$^2$;

an electrically conducting element configured to extend through the intercostal penetration and electrically couple to the defibrillation generator; and a second electrode coupled to the defibrillation generator;

wherein an electric current may be applied between the first and the second electrodes so as to pass through at least a portion of the patient's heart.

61. An electrode for applying an electric current to body tissue in a patient's body cavity, comprising:

a flexible member having a distal conductive surface, a proximal insulating surface and a hole in communication with the distal conductive surface and adapted for coupling to a suction lumen for providing a suction pressure between the distal conductive surface and the body tissue;

wherein the flexible member is movable between a collapsed position in which the flexible member is configured for delivery through a percutaneous penetration into the body cavity and an expanded position in which the distal conductive surface is adapted to contact the body tissue and has a surface area sufficient for applying the electric current to the patient's heart body tissue.

62. A system for applying an electrical charge to body tissue comprising:

an elongate shaft having distal and proximal ends and a longitudinal axis therebetween, the shaft defining an inner lumen having a proximal end adapted for coupling to a source of vacuum;

an electrode coupled to the distal end of the shaft and comprising a flexible member having a distal conductive surface, a proximal insulating surface and a hole in communication with the inner lumen of the shaft and with the distal surface for providing a suction pressure between the distal surface and the patient's heart; and an electrically conducting element coupled to the electrode and having a proximal end adapted for coupling to a source of electrical energy for delivering an electrical charge to the electrode.

63. A method for applying an electrical energy to body tissue comprising:

positioning an electrically conductive surface of a flexible electrode against a surface of the patient's body tissue;

applying a suction pressure between the conductive surface of the flexible member and the body tissue surface to force the conductive surface and the body tissue surfaces together;

positioning a second electrode in contact with the patient's body; and delivering electrical energy between the first and second electrodes such that the electrical energy passes through the patient's body tissue.

64. A method for defibrillating a patient's heart comprising:

contacting a first electrode through a percutaneous penetration against a surface of the patient's heart, the electrode defining an electrically conductive surface having a surface area sufficient for applying a defibrillation voltage to the patient's heart;

contacting a second electrode against the patient's body;

delivering electrical energy through the percutaneous penetration between the first electrode and the second electrode such that the electrical energy passes through at least a portion of the patient's heart, wherein the first and second electrodes are attached to a distal end of an introducer shaft, the introducer shaft being positioned through the percutaneous penetrations; and removing the first electrode from the patient through a percutaneous penetration.

65. A method for defibrillating a patient's heart comprising:

arresting the patient's heart;

performing a surgical procedure on the patient;

introducing a first electrode through a percutaneous penetration in the patient into the thoracic cavity;

moving the first electrode into an expanded configuration;

positioning the first electrode against a surface of the heart;

positioning a second electrode in contact with the patient's body; and delivering electrical energy through the percutaneous penetration between the first electrode and the second electrode such that the electrical energy passes through at least a portion of the patient's heart.

66. A method for defibrillating a patient's heart comprising:

arresting the patient's heart by positioning an occluding member within the ascending aorta to block blood flow therethrough and delivering cardioplegic fluid to the myocardium to paralyze the patient's heart;

introducing a first electrode through a percutaneous penetration in the patient into the thoracic cavity;

moving the first electrode into an expanded configuration;

positioning the first electrode against a surface of the heart;

positioning a second electrode in contact with the patient's body; and delivering electrical energy through the percutaneous penetration between the first electrode and the second electrode such that the electrical energy passes through at least a portion of the patient's heart.

* * * * *